(12) United States Patent
Moldenhauer

(10) Patent No.: US 9,399,778 B2
(45) Date of Patent: Jul. 26, 2016

(54) RICE CULTIVAR CL172

(71) Applicant: BOARD OF TRUSTEES OF THE UNIVERSITY OF ARKANSAS, Little Rock, AR (US)

(72) Inventor: Karen A. K. Moldenhauer, Stuttgart, AR (US)

(73) Assignee: BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 14/538,928

(22) Filed: Nov. 12, 2014

(65) Prior Publication Data

US 2016/0130604 A1    May 12, 2016

(51) Int. Cl.
*A01H 5/10*      (2006.01)
*C12N 15/82*     (2006.01)
*A01H 1/02*      (2006.01)
*A01N 43/50*     (2006.01)

(52) U.S. Cl.
CPC .............. *C12N 15/8274* (2013.01); *A01H 1/02* (2013.01); *A01H 5/10* (2013.01); *A01N 43/50* (2013.01); *C12N 15/8245* (2013.01); *C12N 15/8247* (2013.01); *C12N 15/8275* (2013.01); *C12N 15/8277* (2013.01); *C12N 15/8278* (2013.01); *C12N 15/8279* (2013.01); *C12N 15/8286* (2013.01)

(58) Field of Classification Search
None
See application file for complete search history.

(56) References Cited

U.S. PATENT DOCUMENTS

| | | | |
|---|---|---|---|
| 5,304,719 A | 4/1994 | Segebart | |
| 5,367,109 A | 11/1994 | Segebart | |
| 5,523,520 A | 6/1996 | Hunsperger et al. | |
| 5,763,755 A | 6/1998 | Carlone | |
| 5,850,009 A | 12/1998 | Kevern | |
| 6,956,154 B2 | 10/2005 | Xie | |
| 7,301,083 B2 | 11/2007 | Sarreal et al. | |
| 7,642,434 B2 * | 1/2010 | Moldenhauer | 800/320.2 |
| 8,134,058 B2 * | 3/2012 | Moldenhauer | 800/320.2 |
| 8,288,635 B2 * | 10/2012 | Moldenhauer | 800/320.2 |
| 8,431,805 B2 * | 4/2013 | Moldenhauer | 800/320.2 |
| 8,440,891 B2 * | 5/2013 | Moldenhauer | 800/320.2 |
| 8,440,892 B2 * | 5/2013 | Moldenhauer | 800/320.2 |

OTHER PUBLICATIONS

Bennetzen, et al., 1992, Approaches and progress in the molecular cloning of plant disease resistance genes, *Genetic Engineering*, 14:99-124.

DeBolle, et al., 1996, Antimicrobial peptides from *Mirabilis Jalapa* and *Amaranthus caudatus*: expression, processing, localization and biological activity in transgenic tobacco, *Plant Molec. Biol.*, 31:993-1008.

Eshed, et al., 1996, Less-than-additive epistatic interactions of quantitative trait loci in tomato, *Genetics*, 143:1807-1817.

Kraft, et al., 2000, Linkage disequilibrium and fingerprinting in sugar beet, *Theor. Appl. Genet.*, 101:323-326.

Pang, et al., 1992, Expression of a gene encoding a scorpion insectotoxin peptide in yeast, bacteria and plants, *Gene*, 116:165-172.

Poehlman, J.M. and Sleper, D.A., Breeding Field Crops, 4th Ed. 1995, Iowa State University Press, p. 473.

Smith, C.W. and Dilday, R.H., Origin, Domestication, and Diversification in Rice: Origin, History, Technology, and Production, 2003, John Wiley & Sons, Inc., pp. 4-6.

Yu, et al., 1997, Importance of epistasis as the genetic basis of heterosis in an elite rice hybrid, *Proc. Natl. Acad. Sci.*, 94:9226-9231.

Anonymous, "Horizon Ag rolls out Clearfield for 2010" (online) Oct. 9, 2009, Delta Farm Press; Retrieved from the Internet: URL:http://deltafarmpress.com/rice/horizon-ag-rolls-out-clearfield-2010.

Norman et al. "Grain Yield Response of Fourteen New Rice Cultivars to Nitrogen Fertilization", AAES Research Series; B.R. Wells Rice Research Studies 2009, pp. 166-180, vol. 581.

Robinson, J.C. et al. "Assessment of Disease Reaction of Advanced Southern U.S. Rice Germplasm in the Field", AAES Research Series; B.R. Wells Rice Research Studies 2009, pp. 76-83, vol. 581.

Frizzell, D.L. et al. Development of Degree Day 50 Thermal Unit Thresholds for New Rice Cultivars, AAES Research Series; B.R. Wells Rice Research Studies 2009, pp. 158-165, vol. 581.

Sha X. Y. et al. "Field Evaluation of Imidazolinone-Tolerant Clearfield Rice (*Oryza sativa* L.) at Nine Louisiana Locations", The Plant Genome, Crop Science Society of America, May 31, 2007, pp. 1177-1185, vol. 47, No. 3, Madison, Wisconsin, US.

Kadaru, Suresh et al. Development and application of allele-specific PCR assays for imazethapyr resistance in rice (*Oryza sativa*), Euphytica, Springer, Apr. 2008, pp. 431-438, vol. 160, No. 3.

Webb, B.D. et al. "Utilization characteristics and qualities of United States rice" in Rice grain quality and marketing; IRRI, Manila, Philippines, 1985, pp. 25-35.

U.S. Plant Variety Protection certificate application No. 201500184, Rice CL172, Notice of Allowance dated Jan. 28, 2016.

* cited by examiner

*Primary Examiner* — Medina A Ibrahim
(74) *Attorney, Agent, or Firm* — Jondle & Associates, P.C.

(57) ABSTRACT

A rice cultivar designated CL172 is disclosed. The invention relates to the seeds of rice cultivar CL172, to the plants of rice CL172, to methods for producing a rice plant produced by crossing the cultivar CL172 with itself or another rice variety, and to methods for controlling weeds in the vicinity of plants of rice cultivar CL172, which comprises increased resistance to acetohydroxyacid synthase-inhibiting herbicides. The invention further relates to hybrid rice seeds and plants produced by crossing the cultivar CL172 with another rice cultivar.

41 Claims, No Drawings

RICE CULTIVAR CL172

BACKGROUND OF THE INVENTION

The present invention relates to a new and distinctive rice cultivar, designated CL172. All publications cited in this application are herein incorporated by reference.

Rice is an ancient agricultural crop and is today one of the principal food crops of the world. There are two cultivated species of rice: *Oryza sativa* L., the Asian rice, and *O. glaberrima* Steud., the African rice. *O. sativa* L. constitutes virtually all of the world's cultivated rice and is the species grown in the United States. Three major rice producing regions exist in the United States: the Mississippi Delta (Arkansas, Mississippi, northeast Louisiana, southeast Missouri), the Gulf Coast (southwest Louisiana, southeast Texas), and the Central Valleys of California.

Rice is a semi-aquatic crop that benefits from flooded soil conditions during part or all of the growing season. In the United States, rice is grown on flooded soils to optimize grain yields. Heavy clay soils or silt loam soils with hard pan layers about 30 cm below the surface are typical rice-producing soils because they minimize water losses from soil percolation. Rice production in the United States can be broadly categorized as either dry-seeded or water-seeded. In the dry-seeded system, rice is sown into a well-prepared seed bed with a grain drill or by broadcasting the seed and incorporating it with a disk or harrow. Moisture for seed germination is from irrigation or rainfall. For the dry-seeded system, when the plants have reached sufficient size (four- to five-leaf stage), a shallow permanent flood of water 5 to 16 cm deep is applied to the field for the remainder of the crop season.

In the water-seeded system, rice seed is soaked for 12 to 36 hours to initiate germination, and the seed is broadcast by airplane into a flooded field. The seedlings emerge through a shallow flood, or the water may be drained from the field for a short period of time to enhance seedling establishment. A shallow flood is maintained until the rice approaches maturity. For both the dry-seeded and water-seeded production systems, the fields are drained when the crop is mature, and the rice is harvested 2 to 3 weeks later with large combines. In rice breeding programs, breeders try to employ the production systems predominant in their respective region. Thus, a drill-seeded breeding nursery is used by breeders in a region where rice is drill-seeded and a water-seeded nursery is used in regions where water-seeding is important.

Rice in the United States is classified into three primary market types by grain size, shape, and chemical composition of the endosperm: long-grain, medium grain and short-grain. Typical U. S. long-grain cultivars cook dry and fluffy when steamed or boiled, whereas medium- and short-grain cultivars cook moist and sticky. Long-grain cultivars have been traditionally grown in the southern states and generally receive higher market prices.

Rice, *Oryza sativa* L., is an important and valuable field crop. Thus, a continuing goal of plant breeders is to develop stable, high yielding rice cultivars that are agronomically sound. The reasons for this goal are obviously to maximize the amount of grain produced on the land used and to supply food for both animals and humans. To accomplish this goal, the rice breeder must select and develop rice plants that have the traits that result in superior cultivars.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary and illustrative, not limiting in scope. In various embodiments, one or more of the above described problems have been reduced or eliminated, while other embodiments are directed to other improvements.

According to the invention, there is provided a novel rice cultivar designated CL172. This invention thus relates to the seeds of rice cultivar CL172, to the plants of rice CL172 and to methods for producing a rice plant produced by crossing the rice CL172 with itself or another rice line.

Thus, any such methods using the rice variety CL172 are part of this invention: selfing, backcrosses, hybrid production, crosses to populations, and the like. All plants produced using rice variety CL172 as a parent are within the scope of this invention. Advantageously, the rice variety could be used in crosses with other, different, rice plants to produce first generation ($F_1$) rice hybrid seeds and plants with superior characteristics.

In another aspect, the present invention provides for single gene converted plants of CL172. The single transferred gene may preferably be a dominant or recessive allele. Preferably, the single transferred gene will confer such traits as herbicide resistance, insect resistance, resistance for bacterial, fungal, or viral disease, male fertility, male sterility, enhanced nutritional quality, and industrial usage. The single gene may be a naturally occurring rice gene or a transgene introduced through genetic engineering techniques.

In another aspect, the present invention provides regenerable cells for use in tissue culture of rice plant CL172. The tissue culture will preferably be capable of regenerating plants having the physiological and morphological characteristics of the foregoing rice plant, and of regenerating plants having substantially the same genotype as the foregoing rice plant. Preferably, the regenerable cells in such tissue cultures will be embryos, protoplasts, meristematic cells, callus, pollen, leaves, anthers, root tips, flowers, seeds, panicles or stems. Still further, the present invention provides rice plants regenerated from the tissue cultures of the invention.

In one aspect, the present invention provides methods for controlling weeds or undesired vegetation in the vicinity of a plant of rice cultivar CL172. One method comprises applying an effective amount of an acetohydroxyacid synthase (AHAS)-inhibiting herbicide, particularly an imidazolinone herbicide, to the weeds and to a plant of rice cultivar CL172. Another method comprises contacting a seed of rice cultivar CL172 before sowing and/or after pregermination with an effective amount of an AHAS-inhibiting herbicide, particularly an imidazolinone herbicide. The present invention further provides seeds of rice cultivar CL172 treated with an effective amount of an AHAS-inhibiting herbicide, particularly an imidazolinone herbicide.

In addition to the exemplary aspects and embodiments described above, further aspects and embodiments will become apparent by study of the following descriptions.

DETAILED DESCRIPTION OF THE INVENTION

In the description and tables which follow, a number of terms are used. In order to provide a clear and consistent understanding of the specification and claims, including the scope to be given such terms, the following definitions are provided:

Abiotic stress. As used herein, abiotic stress relates to all non-living chemical and physical factors in the environment. Examples of abiotic stress include, but are not limited to, drought, flooding, salinity, temperature, and climate change.

Aggregate sheath spot. Is caused by the fungus *Rhizoctonia oryzae-sativae* (Sawada) Mordue (=*Ceratobasidium oryzae-sativae*). This disease causes sheath lesions and can reduce yield and grain quality. California varieties generally rate between 2 and 4 in greenhouse tests on a scale of 0 to 4.

Alkali spreading value. Indicator of gelatinization temperature and an index that measures the extent of disintegration of milled rice kernel in contact with dilute alkali solution. Standard long grains have 3 to 5 Alkali Spreading Value (intermediate gelatinization temperature). Standard medium and short grain rice have 6 to 7 Alkali Spreading Values (low gelatinization temperature).

Allele. Allele is any of one or more alternative forms of a gene, all of which alleles relate to one trait or characteristic. In a diploid cell or organism, the two alleles of a given gene occupy corresponding loci on a pair of homologous chromosomes.

Alter. The utilization of up-regulation, down-regulation, or gene silencing.

Apparent amylose percent. The most important grain characteristic that describes cooking behavior in each grain class, or type, i.e., long, medium and short grain. The percentage of the endosperm starch of milled rice that is amylose. Standard long grains contain 20 to 23% amylose. Rexmont type long grains contain 24 to 25% amylose. Short and medium grain rice contain 16 to 19% amylose. Waxy rice contains 0% amylose. Amylose values will vary over environments.

Backcrossing. Backcrossing is a process in which a breeder repeatedly crosses hybrid progeny back to one of the parents, for example, a first generation hybrid $F_1$ with one of the parental genotypes of the $F_1$ hybrid.

Bakanae. Is caused by the fungus *Fusarium fujikuroi* Nirenberg (=*Gibberella fujikuroi*). It causes reduced seed germination and abnormal seedling elongation often followed by crown rot. Susceptibility of varieties is expressed as percent symptomatic plants.

Blanking %. Visual estimate of the percent of sterile florets (florets that are empty with no filled kernels) in the panicle as a measurement of cool temperature induced pollen sterility. Blanking may also be induced by high temperatures and by genetic incompatibility of the parents. This data may be collected in screening nurseries at cool locations, cool years, and also in screening tests in refrigerated greenhouses.

Breakdown. The peak viscosity minus the hot paste viscosity.

Breeding. The genetic manipulation of living organisms.

Cell. Cell as used herein includes a plant cell, whether isolated, in tissue culture or incorporated in a plant or plant part.

Cross-pollination. Fertilization by the union of two gametes from different plants.

Cool paste viscosity. Viscosity measure of rice flour/water slurry after being heated to 95EC and uniformly cooled to 50EC (American Association of Cereal Chemist). Values less than 200 for cool paste indicate softer cooking types of rice.

Days to 50% heading. Average number of days from planting to the day when 50% of all panicles are exerted at least partially through the leaf sheath. A measure of maturity.

Diploid. A cell or organism having two sets of chromosomes.

Elongation. Cooked kernel elongation is the ratio of the cooked kernel length divided by the uncooked kernel length. Extreme cooked kernel elongation is a unique feature of basmati type rice and an important quality criterion for that market type.

Embryo. The embryo is the small plant contained within a mature seed.

Essentially all the physiological and morphological characteristics. A plant having essentially all the physiological and morphological characteristics means a plant having the physiological and morphological characteristics of the cultivar, except for the characteristics derived from the converted gene.

F#. The "F" symbol denotes the filial generation, and the # is the generation number, such as $F_1$, $F_2$, $F_3$, etc.

Final viscosity. Viscosity at the end of the test or cold paste.

Gene. As used herein, "gene" refers to a unit of inheritance corresponding to DNA or RNA that code for a type of protein or for an RNA chain that has a function in the organism.

Gene silencing. The interruption or suppression of the expression of a gene at the level of transcription or translation.

Genotype. Refers to the genetic constitution of a cell or organism.

Grain length (L). Length of a rice grain is measured in millimeters.

Grain width (W). Width of a rice grain is measured in millimeters.

Grain yield. Grain yield is measured in pounds per acre and at 12.0% moisture. Grain yield of rice is determined by the number of panicles per unit area, the number of fertile florets per panicle, and grain weight per floret.

Haploid. A cell or organism having one set of the two sets of chromosomes in a diploid.

Harvest moisture. The percent of moisture of the grain when harvested.

Head rice. Unbroken kernels of milled rice.

Hot paste viscosity. Viscosity measure of rice flour/water slurry after being heated to 95EC. Lower values indicate softer and stickier cooking types of rice.

Length/Width (L/W) ratio. This ratio is determined by dividing the average length (L) by the average width (W).

Linkage. Refers to a phenomenon wherein alleles on the same chromosome tend to segregate together more often than expected by chance if their transmission was independent.

Linkage disequilibrium. Refers to a phenomenon wherein alleles tend to remain together in linkage groups when segregating from parents to offspring, with a greater frequency than expected from their individual frequencies.

Locus. A defined segment of DNA.

Lodging resistance (also called Straw strength). Lodging is measured as a subjective rating and is percentage of the plant stems leaning or fallen completely to the ground before harvest. Visual scoring where 0%=all plants standing to 100%=all plant in plot are laying flat on the soil surface. Lodged plants are difficult to harvest and reduce yield and grain quality.

Milling yield. Milling yield is the total amount of milled rice (whole and broken kernels) recovered after removal of hulls, bran, and germ by milling and head-rice yield, the total amount of whole kernels recovered after milling. Values are expressed as weight percentage of the original paddy or rough rice sample that was milled. For example, a milling yield of 65/70 is a sample of 100 grams of rough rice that produced 65 grams of head rice and 70 grams of total milled rice.

Nucleic acid. An acidic, chainlike biological macromolecule consisting of multiple repeat units of phosphoric acid, sugar and purine and pyrimidine bases.

1000 Grain wt. The weight of 1000 rice grains as measured in grams. It can be for paddy, brown or milled rice.

Pedigree. Refers to the lineage or genealogical descent of a plant.

Pedigree distance. Relationship among generations based on their ancestral links as evidenced in pedigrees. May be measured by the distance of the pedigree from a given starting point in the ancestry.

Percent identity. Percent identity as used herein refers to the comparison of the homozygous alleles of two rice varieties. Percent identity is determined by comparing a statistically significant number of the homozygous alleles of two developed varieties. For example, a percent identity of 90% between rice variety 1 and rice variety 2 means that the two varieties have the same allele at 90% of their loci.

Percent similarity. Percent identity as used herein refers to the comparison of the homozygous alleles of two rice varieties. Percent identity is determined by comparing a statistically significant number of the homozygous alleles of two developed varieties. For example, a percent identity of 90% between rice variety 1 and rice variety 2 means that the two varieties have the same allele at 90% of their loci.

Peak viscosity. The maximum viscosity attained during heating when a standardized instrument-specific protocol is applied to a defined rice flour-water slurry.

Plant. As used herein, the term "plant" includes reference to an immature or mature whole plant, including a plant from which seed, grain, or anthers have been removed. Seed or embryo that will produce the plant is also considered to be the plant.

Plant height. Plant height measured in centimeters or inches is taken from soil surface to the tip of the extended panicle at harvest.

Plant parts. As used herein, the term "plant parts" (or a rice plant, or a part thereof) includes but is not limited to protoplasts, leaves, stems, roots, root tips, anthers, pistils, seed, grain, embryo, pollen, ovules, cotyledon, hypocotyl, pod, flower, shoot, tissue, petiole, cells, meristematic cells, and the like.

Progeny. As used herein, includes an $F_1$ rice plant produced from the cross of two rice plants where at least one plant includes rice cultivar CL172 and progeny further includes, but is not limited to, subsequent $F_2$, $F_3$, $F_4$, $F_5$, $F_6$, $F_7$, $F_8$, $F_9$, and $F_{10}$ generational crosses with the recurrent parental line.

Quantitative Trait Loci (QTL). Quantitative trait loci (QTL) refer to genetic loci that control to some degree numerically representable traits that are usually continuously distributed.

RVA viscosity. Rapid Visco Analyzer is a widely used laboratory instrument to examine paste viscosity, or thickening ability of milled rice during the cooking process.

RVU. The RVA scale is measured in RVUs. This is the native viscosity unit of the RVA. 1 RVU is equivalent to 12 CP. CP equals "centipoises" which equals unit of viscosity (kg $s^{-1}m^{-1}$) and 1 kg $s^{-1}m^{-1}$ equals 1000 centipoises.

Regeneration. Regeneration refers to the development of a plant from tissue culture.

Setback. Setback 1 is the final viscosity minus trough viscosity. Setback 2 is the final viscosity minus peak viscosity and is what is most commonly referred to for rice quality testing.

Single gene converted (Conversion). Single gene converted (conversion), also known as coisogenic plants, refers to plants which are developed by a plant breeding technique called backcrossing wherein essentially all of the desired morphological and physiological characteristics of a variety are recovered in addition to the single gene transferred into the variety via the backcrossing technique or via genetic engineering.

Stem rot. Is caused by the fungus *Sclerotium oryzae* Cattaneo (=*Magnaporthe salvinii*). It produces sheath and stem lesions that can reduce yield and grain quality. California varieties are generally rated between 4.5 and 7.5 on a scale of 0 to 10.

Trough viscosity. The minimum viscosity after the peak, normally occurring when the sample starts to cool.

Rice cultivar CL172 originated from the cross 248Drew16C-1-3/6/LaGrue//Katy/Starbonnet/5/Newbonnet/Katy//RA73/Lemont/4/Lebonnet/CI9902/3/Dawn/CI9695//Starbonnet made in Stuttgart, Ark. in 2007. Drew, also known as RU9201176, (US Plant Variety Protection certificate 9700138) is a blast resistant good yielding long-grain described by Moldenhauer et al., 1998. LaGrue is a high yielding long-grain rice described by Moldenhauer et al. 1994. Katy (Moldenhauer et al., 1990) is a blast resistant cultivar, and Starbonnet (Johnston et al. 1968) is a long grain cultivar. Newbonnet is a high yielding cultivar (Johnston et al.). Lemont (Bollich et al., 1985) is a high yielding, midseason, long-grain, semidwarf cultivar which is very susceptible to sheath blight, released in 1983. Lebonnet (Bollich et al., 1975) released in 1974, is a large kernel, long-grain cultivar. CI 9902 is a short stature, lodging resistant, rice blast resistant, long-grain selection developed at Crowley, La., and has the pedigree 'Dawn'/245717/3/13-D//'Rexoro'/Unknown. Dawn (Bollich et al., 1968) is a blast resistant, long-grain gold hulled cultivar widely used in crosses. CI9695 has the pedigree CI9453/CI9187//'Bluebonnet 50'. Rexoro and Bluebonnet 50 were described by Johnston in 1958. The experimental designation for early evaluation of CL172 was STG10IMI-01-096, starting with a bulk of F4 seed from the 2010 panicle row IMI-01-096, and was later given the experimental designation RU1201102. Rice cultivar CL172 was tested in the Arkansas Rice Performance Trials (ARPT) and the Cooperative Uniform Regional Rice Nursery (URRN) during 2012-2013 as entry RU1201102.

Rice cultivar CL172 is a very high-yielding, short season, long-grain Clearfield rice cultivar with maturity similar to rice cultivar CL151 and CL152. Plants of CL172 have erect culms, green erect leaves and glaborus lemma, palea, and leaf blades. The lemma and palea are straw colored with red apiculi after full heading, most of which fade to straw at maturity.

Kernels of CL172 are the desired long-grain size averaging 7.28 mm for the 5 locations of the 2012 Arkansas Rice Performance Trials (ARPT) compared to CL111, CL151, and CL152 at 7.09, 6.77, and 6.72 mm/kernel, respectively. Individual milled kernel weights of CL172, CL111, CL151, and CL152 averaged 21.1, 20.5, 19.7 and 17.4 mg/kernel, respectively, in the ARPT 2012. Rice cultivar CL172 has lower levels of chalky kernels at 0.70% than the CL151 or CL152 at 2.00 and 1.35%, respectively, according to Riceland Foods Inc. Laboratory from the 2012 ARPT samples. The USDA-ARS Dale Bumpers National Rice Research Center's winseedle screening of the Cooperative Uniform Regional Rice Nursery (URRN) in 2013 also showed a lower chalk for CL172 at 2.63% compared to CL151 and CL152 at 11.22 and 8.64%, respectively.

CL172 is a semi-dwarf cultivar approximately 37 inches in height with strong straw strength which is an indicator of lodging resistance and in 2012 and 2013 in ARPT and URRN it did not lodge. On a relative straw strength scale (0=very strong straw, 9=very weak straw), rice cultivars CL172, CL151, CL152, Francis, Wells, and Roy J rated 1.0, 2.7, 1.7, 2.3, 2.3, and 1.0, respectively.

Rice cultivar CL172 is resistant to common rice blast (*Pyricularia grisea* (Cooke) Sacc) races IB-1, IB-49, IB-54, IC-1, IC-17, ID-13, IE-1, and IG-1, with summary ratings in greenhouse tests for 2012-2013 of 0, 0, 0, 0, 2, 0, 0, and 0, respectively, using the standard disease scale of 0=immune, 9=maximum disease susceptibility.

The rough rice grain yields of rice cultivar CL172 have consistently ranked as one of the highest in the Arkansas Rice Performance Trials (ARPT). In 11 ARPT tests (2012-2013), CL172, CL111, CL151, CL152, CLXL729, CLXL745, Roy J, Francis, Wells, and LaKast averaged yields of 201, 178, 192, 176, 201, 191, 219, 205, 198, and 204 bushels/acre, respectively. Data from the URRN conducted at Stuttgart, Ark., Crowley, La., Stoneville, Miss., Campbell, Mo., and Beaumont, Tex. during 2012-2013 showed that CL172 average grain yield of 197 bushels/acre compared favorably with those of CL111, CL151, CL152, Roy J, Francis, Wells, and LaKast, at 202, 208, 182, 204, 194, 194 and 217 bushels/acre, respectively.

Milling yields (mg g$^{-1}$ whole kernel:mg g$^{-1}$ total milled rice) at 120 mg g$^{-1}$ moisture from the ARPT, 2012-2013, averaged 640:700, 620:700, 640:700, 640:700, 640:710, 640:710, 580:700 and 610:710, for CL172, CL111, CL151, CL152, Roy J, Francis, Wells, and LaKast, respectively. Milling yields for the URRN during the same period of time, 2012-2013, averaged 610:700, 620:701, 610:710, 610:710, 560:700, 590:710, 570:710 and 590:710, for CL172, CL111, CL151, CL152, Roy J, Francis, Wells, and LaKast, respectively.

The endosperm of rice cultivar CL172 is nonglutinous, nonaromatic, and covered by a light brown pericarp. Rice quality parameters indicate that CL172 has typical southern U.S. long-grain rice cooking quality characteristics as described by Webb et al. 1985. Rice cultivar CL172 has an average apparent starch amylose content of 21.7 g kg$^{-1}$ and an intermediate gelatinization temperature (70-75° C.), as indicated by an average alkali (17 g kg$^{-1}$ KOH) spreading reaction of 3 to 5.

Rice cultivar CL172 has shown uniformity and stability as described in the following variety description information. It has been self-pollinated a sufficient number of generations with careful attention to uniformity of plant type. The line has been increased with continued observation for uniformity.

Rice cultivar CL172 has the following morphologic and other characteristics (based primarily on data collected in Arkansas).

TABLE 1

VARIETY DESCRIPTION INFORMATION

Plant:

Grain type: Long
Days to maturity (50% heading): 86
Plant height: 91.0 cm
Plant color (at booting): Green
Culm:

Angle (degrees from perpendicular after flowering): Erect (less than 30° C.)
Flag leaf (after heading):

Pubescence: Glabrous
Leaf angle (after heading): Erect to intermediate
Blade color (at heading): Green to dark green TABLE 1-continued

VARIETY DESCRIPTION INFORMATION

Panicle:

Length: 21.0 cm
Type: Intermediate
Exertion (near maturity): Moderately well
Axis: Droopy
Shattering (at maturity): Low (1%-5%)
Grain (spikelet):

Awns (after full heading): Short and partly awned and long and partly awned
Apiculus color (at full heading): Red
Apiculus color (at maturity): Straw
Stigma color: White and some light purple
Lemma and palea color (at maturity): Straw
Lemma and palea pubescence: Glabrous
Grain (seed):

Seed coat color: Light brown
Endosperm type: Nonglutinous
Scent: Nonscented
Shape class (length/width ratio):

Paddy: Long (3.4:1 and more)
Brown: Long (3.4:1 and more)
Milled: Long (3.0:1 and more)
Size: 21.1 g/1000 seeds milled rice
Starch amylose content: 21.7 g kg$^{-1}$
Alkali spreading value: 3 to 5 (17 g kg$^{-1}$ KOH Solution)
Gelatinization temperature type: Intermediate (70° C. to 75° C.)
Disease resistance:

Rice blast (*Pyricularia grisea* (Cooke) Sacc.) races IB-1, IB-49, IB-54, IC-1, IC-17, ID-13, IE-1, IG-1: Resistant
Straighthead (physiological disorder): Susceptible
Kernel smut (*Tilletia barclayana* (Bref.) Sacc. & Syd. in Sacc.): Susceptible
Sheath blight (*Rhizoctonia solani* Kuhn): Susceptible
False smut (*Ustilaginoidea vixens* (Cooke) Takah.): Susceptible
Bacterial panicle blight (*Burkholderia glumae* and *B. gladioli*): Susceptible
Herbicide resistance: Imidazolinones Rice cultivar CL172 is particularly distinguished by the following characteristics: resistant to AHAS-inhibiting herbicides, particularly an imidizolinine herbicide; contains the Pi-ta gene for blast resistance; an erect semidwarf stature; longer kernels than CL151 or CL152; and a high yield potential, good milling and clear translucent kernels.

This invention also is directed to methods for producing a rice plant by crossing a first parent rice plant with a second parent rice plant wherein either the first or second parent rice plant is a rice plant of the line CL172. Further, both first and second parent rice plants can come from the rice cultivar CL172. Still further, this invention also is directed to methods for producing a rice cultivar CL172-derived rice plant by crossing rice cultivar CL172 with a second rice plant and growing the progeny seed, and repeating the crossing and growing steps with the rice cultivar CL172-derived plant from 0 to 7 times. Thus, any such methods using the rice cultivar CL172 are part of this invention: selfing, backcrosses, hybrid production, crosses to populations, and the like. All plants produced using rice cultivar CL172 as a parent are within the scope of this invention, including plants derived from rice cultivar CL172. Advantageously, the rice cultivar is used in crosses with other, different, rice cultivars to produce first generation (F$_1$) rice seeds and plants with superior characteristics.

It should be understood that the cultivar can, through routine manipulation of cytoplasmic or other factors, be produced in a male-sterile form. Such embodiments are also contemplated within the scope of the present claims.

As used herein, the term plant includes plant cells, plant protoplasts, plant cell tissue cultures from which rice plants can be regenerated, plant calli, plant clumps and plant cells that are intact in plants or parts of plants, such as embryos, pollen, ovules, flowers, glumes, panicles, leaves, stems, roots, root tips, anthers, pistils and the like.

Further Embodiments of the Invention

Methods for Controlling Weeds Using the Present Invention:

The plants of rice cultivar CL172 have increased tolerance or resistance to AHAS-inhibiting herbicides, particularly imidazolinone herbicides. Thus, the plants of rice cultivar CL172 are herbicide-tolerant or herbicide-resistant rice plants. An "herbicide-tolerant" or a "herbicide-resistant" rice plant is a rice plant that is tolerant or resistant to at least one herbicide at a level that would normally kill, or inhibit the growth of, a normal or wild-type rice plant. For the present invention, the terms "herbicide-tolerant" and "herbicide-resistant" are used interchangeably and are intended to have an equivalent meaning and an equivalent scope. Similarly, the terms "herbicide-tolerance" and "herbicide-resistance" are used interchangeably and are intended to have an equivalent meaning and an equivalent scope. Likewise, the terms "imidazolinone-tolerant" and "imidazolinone-resistant" are used interchangeably and are intended to be of an equivalent meaning and an equivalent scope as the terms "imidazolinone-tolerance" and "imidazolinone-resistance", respectively.

The plants of rice cultivar CL172 have increased resistance to AHAS-inhibiting herbicides, particularly imidazolinone herbicides, and thus find use in methods for controlling weeds. Accordingly, the present invention provides a method for controlling weeds in the vicinity of a rice plant of the invention. The method comprises applying an effective amount of an herbicide to the weeds and to the rice plant of the present invention.

For the methods of the present invention, the preferred amount or concentration of the herbicide is an "effective amount" or "effective concentration." "Effective amount" and "effective concentration" is intended to be an amount and concentration, respectively, that is sufficient to kill or inhibit the growth of a similar, wild-type, rice plant, rice plant tissue, rice plant cell, or rice seed, but that said amount does not kill or inhibit as severely the growth of the herbicide-resistant plants, plant tissues, plant cells, and seeds of the present invention. Typically, the effective amount of an herbicide is an amount that is routinely used in agricultural production systems to kill weeds of interest. Such an amount is known to those of ordinary skill in the art.

By "similar, wild-type, plant, plant tissue, plant cell or seed" is intended to be a plant, plant tissue, plant cell, or seed, respectively, that lacks the herbicide-resistance characteristics and/or particular polynucleotide of the invention that are disclosed herein. The use of the term "wild-type" is not, therefore, intended to imply that a plant, plant tissue, plant cell, or other seed lacks recombinant DNA in its genome, and/or does not possess herbicide resistant characteristics that are different from those disclosed herein.

The present invention provides methods for controlling weeds or undesired vegetation in the vicinity of plants of rice cultivar CL172. The methods involve applying an effective amount of at least one herbicide that interferes with the activity of the AHAS enzyme. Herbicides that are known to interfere with or inhibit the activity of the wild-type AHAS enzyme are known as AHAS-inhibiting herbicides, and include, for example, imidazolinone herbicides, sulfonylurea herbicides, triazolopyrimidine herbicides, pyrimidinyloxybenzoate herbicides, sulfonylamino-carbonyltriazolinone herbicides, and mixtures thereof. Preferably, for the present invention, the AHAS-inhibiting herbicide is an imidazolinone herbicide, or a mixture of two or more imidazolinone herbicides.

For the present invention, the imidazolinone herbicides include, but are not limited to, PURSUIT (imazethapyr), NEWPATH (imazethapyr), BEYOND (imazamox), CADRE (imazapic), RAPTOR (imazamox), SCEPTER (imazaquin), ASSERT (imazethabenz), ARSENAL (imazapyr), a derivative of any of the aforementioned herbicides, and a mixture of two or more of the aforementioned herbicides, for example, imazapyr/imazamox (ODYSSEY). More specifically, the imidazolinone herbicide can be selected from, but is not limited to, 2-(4-isopropyl-4-methyl-5-oxo-2-imidiazolin-2-yl)-nicotinic acid, [2-(4-isopropyl)-4-][methyl-5-oxo-2-imidazolin-2-yl)-3-quinolinecarboxylic] acid, [5-ethyl-2-(4-isopropyl-]4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, [2-(4-isopropyl-4-methyl-5-oxo-2-]imidazolin-2-yl)-5-methylnicotinic acid, and a mixture of methyl[6-(4-isopropyl-4-]methyl-5-oxo-2-imidazolin-2-yl)-m-toluate and methyl[2-(4-isopropyl-4-methyl-5-]oxo-2-imidazolin-2-yl)-p-toluate. The use of 5-ethyl-2-(4-isopropyl-4-methyl-5-oxo-2-imidazolin-2-yl)-nicotinic acid and [2-(4-isopropyl-4-methyl-5-oxo-2-imidazolin-2-]yl)-5-(methoxymethyl)-nicotinic acid is preferred. The use of [2-(4-isopropyl-4-]methyl-5-oxo-2-imidazolin-2-yl)-5-(methoxymethyl)-nicotinic acid is particularly preferred.

For the present invention, the sulfonylurea herbicides include, but are not limited to, chlorsulfuron, metsulfuron methyl, sulfometuron methyl, chlorimuron ethyl, thifensulfuron methyl, tribenuron methyl, bensulfuron methyl, nicosulfuron, ethametsulfuron methyl, rimsulfuron, triflusulfuron methyl, triasulfuron, primisulfuron methyl, cinosulfuron, amidosulfiuon, fluzasulfuron, imazosulfuron, pyrazosulfuron ethyl, halosulfuron, azimsulfuron, cyclosulfuron, ethoxysulfuron, flazasulfuron, flupyrsulfuron methyl, foramsulfuron, iodosulfuron, oxasulfuron, mesosulfuron, prosulfuron, sulfosulfuron, trifloxysulfuron, tritosulfuron, a derivative of any of the aforementioned herbicides, and a mixture of two or more of the aforementioned herbicides.

The triazolopyrimidine herbicides of the invention include, but are not limited to, cloransulam, diclosulam, florasulam, flumetsulam, metosulam, and penoxsulam.

The pyrimidinyloxybenzoate herbicides of the invention include, but are not limited to, bispyribac, pyrithiobac, pyriminobac, pyribenzoxim and pyriftalid. The sulfonylamino-carbonyltriazolinone herbicides include, but are not limited to, flucarbazone and propoxycarbazone.

It is recognized that pyrimidinyloxybenzoate herbicides are closely related to the pyrimidinylthiobenzoate herbicides and are generalized under the heading of the latter name by the Weed Science Society of America. Accordingly, the herbicides of the present invention further include pyrimidinylthiobenzoate herbicides, including, but not limited to, the pyrimidinyloxybenzoate herbicides described above.

By providing rice plants having increased resistance to herbicides, particularly AHAS-inhibiting herbicides, a wide variety of formulations can be employed for protecting plants from weeds, so as to enhance plant growth and reduce competition for nutrients. An herbicide can be used by itself for pre-emergence, post-emergence, pre-planting and at planting to control weeds in areas surrounding the rice plants described herein, or an imidazolinone herbicide formulation can be used that contains other additives. The herbicide can also be used as a seed treatment. Additives found in an imidazolinone herbicide formulation include other herbicides, detergents, adjuvants, spreading agents, sticking agents, stabilizing agents, or the like. The herbicide formulation can be a wet or dry preparation and can include, but is not limited to, flowable powders, emulsifiable concentrates and liquid concentrates. The herbicide and herbicide formulations can be applied in accordance with conventional methods, for example, by spraying, irrigation, dusting, or the like.

The present invention provides methods that involve the use of at least one AHAS-inhibiting herbicide selected from the group consisting of imidazolinone herbicides, sulfonylurea herbicides, triazolopyrimidine herbicides, pyrimidinyloxybenzoate herbicides, sulfonylamino-carbonyltriazolinone herbicides, and mixtures thereof. In these methods, the AHAS-inhibiting herbicide can be applied by any method known in the art including, but not limited to, seed treatment, soil treatment, and foliar treatment.

Prior to application, the AHAS-inhibiting herbicide can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner (see, e.g., for review, U.S. Pat. No. 3,060,084, EP-A 707 445 (for liquid concentrates), Browning, "Agglomeration", Chemical Engineering, pp. 147-48 (Dec. 4, 1967); Perry's Chemical Engineer's Handbook, 4th Ed., McGraw-Hill, New York, pp. 8-57 (1963), and et seq.; PCT Publication No. WO 91/13546; U.S. Pat. Nos. 4,172,714; 4,144,050; 3,299,566; 3,920,442; 5,180,587; 5,232,701; and 5,208,030; G.B. Patent No. 2,095,558; Klingman, "Weed Control as a Science", John Wiley and Sons, Inc., New York (1961); Hance et al., Weed Control Handbook, 8th Ed., Blackwell Scientific Publications, Oxford (1989); Mollet, H., Grubemann, A., Formulation technology, Wiley VCH Verlag GmbH, Weinheim, Germany (2001); and D. A. Knowles, Chemistry and Technology of Agrochemical Formulations, Kluwer Academic Publishers (ISBN 0-7514-0443-8), Dordrecht (1998)), for example by extending the active compound with auxiliaries suitable for the formulation of agrochemicals, such as solvents and/or carriers, if desired, emulsifiers, surfactants and dispersants, preservatives, antifoaming agents, anti-freezing agents, for seed treatment formulation, also optionally colorants and/or binders and/or gelling agents.

Examples of suitable solvents are water, aromatic solvents (for example, Solvesso products, xylene), paraffins (for example, mineral oil fractions), alcohols (for example, methanol, butanol, pentanol, benzyl alcohol), ketones (for example, cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used.

Examples of suitable carriers are ground natural minerals (for example, kaolins, clays, talc, chalk) and ground synthetic minerals (for example, highly disperse silica, silicates).

Suitable emulsifiers are nonionic and anionic emulsifiers (for example, polyoxyethylene fatty alcohol ethers, alkylsulfonates and arylsulfonates).

Examples of dispersants are lignin-sulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as, kerosene or diesel oil, furthermore coal tar oils and oils of vegetable or animal origin, aliphatic, cyclic and aromatic hydrocarbons, for example, toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example, dimethyl sulfoxide, N-methylpyrrolidone or water.

Also anti-freezing agents such as glycerin, ethylene glycol, propylene glycol and bactericides such as can be added to the formulation.

Suitable antifoaming agents are for example antifoaming agents based on silicon or magnesium stearate.

Suitable preservatives are for example Dichlorophen and enzylalkoholhemiformal.

Seed treatment formulations may additionally comprise binders and optionally colorants.

Binders can be added to improve the adhesion of the active materials on the seeds after treatment. Suitable binders are block copolymers EO/PO surfactants but also polyvinylalcohols, polyvinylpyrrolidones, polyacrylates, polymethacrylates, polybutenes, polyisobutylenes, polystyrene, polyethyleneamines, polyethyleneamides, polyethyleneimines (Lupasol, Polymin), polyethers, polyurethans, polyvinylacetate, tylose and copolymers derived from these polymers.

Optionally, colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

An example of a suitable gelling agent is carrageen (Satiagel).

Powders, materials for spreading, and dustable products can be prepared by mixing or concomitantly grinding the active substances with a solid carrier.

Granules, for example, coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01% to 95% by weight, preferably from 0.1 to 90% by weight, of the AHAS-inhibiting herbicide. In this case, the AHAS-inhibiting herbicides are employed in a purity of 90% to 100% by weight, preferably 95% to 100% by weight (according to NMR spectrum). For seed treatment purposes, respective formulations can be diluted 2-10 fold leading to concentrations in the ready to use preparations of 0.01% to 60% by weight active compound by weight, preferably 0.1 to 40% by weight.

The AHAS-inhibiting herbicide can be used as such, in the form of their formulations or the use forms prepared therefrom, for example, in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the AHAS-inhibiting herbicide according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001% to 10%, preferably from 0.01% to 1% per weight.

The AHAS-inhibiting herbicide may also be used successfully in the ultra-low-volume process (ULV), it being possible to apply formulations comprising over 95% by weight of active compound, or even to apply the active compound without additives.

The following are examples of formulations:
1. Products for dilution with water for foliar applications. For seed treatment purposes, such products may be applied to the seed diluted or undiluted.

A. Water-soluble concentrates (SL, LS). Ten parts by weight of the AHAS-inhibiting herbicide are dissolved in 90 parts by weight of water or a water-soluble solvent. As an alternative, wetters or other auxiliaries are added. The AHAS-inhibiting herbicide dissolves upon dilution with water, whereby a formulation with 10% (w/w) of AHAS-inhibiting herbicide is obtained.

B. Dispersible concentrates (DC). Twenty parts by weight of the AHAS-inhibiting herbicide are dissolved in 70 parts by weight of cyclohexanone with addition of 10 parts by weight of a dispersant, for example polyvinylpyrrolidone. Dilution with water gives a dispersion, whereby a formulation with 20% (w/w) of AHAS-inhibiting herbicide is obtained.

C. Emulsifiable concentrates (EC). Fifteen parts by weight of the AHAS-inhibiting herbicide are dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of AHAS-inhibiting herbicide is obtained.

D. Emulsions (EW, EO, ES). Twenty-five parts by weight of the AHAS-inhibiting herbicide are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g., Ultraturrax) and made into a homogeneous emulsion. Dilution with water gives an emulsion, whereby a formulation with 25% (w/w) of AHAS-inhibiting herbicide is obtained.

E. Suspensions (SC, OD, FS). In an agitated ball mill, 20 parts by weight of the AHAS-inhibiting herbicide are comminuted with addition of 10 parts by weight of dispersants, wetters and 70 parts by weight of water or of an organic solvent to give a fine AHAS-inhibiting herbicide suspension. Dilution with water gives a stable suspension of the AHAS-inhibiting herbicide, whereby a formulation with 20% (w/w) of AHAS-inhibiting herbicide is obtained.

F. Water-dispersible granules and water-soluble granules (WG, SG). Fifty parts by weight of the AHAS-inhibiting herbicide are ground finely with addition of 50 parts by weight of dispersants and wetters and made as water-dispersible or water-soluble granules by means of technical appliances (for example, extrusion, spray tower, fluidized bed). Dilution with water gives a stable dispersion or solution of the AHAS-inhibiting herbicide, whereby a formulation with 50% (w/w) of AHAS-inhibiting herbicide is obtained.

G. Water-dispersible powders and water-soluble powders (WP, SP, SS, WS). Seventy-five parts by weight of the AHAS-inhibiting herbicide are ground in a rotor-stator mill with addition of 25 parts by weight of dispersants, wetters and silica gel. Dilution with water gives a stable dispersion or solution of the AHAS-inhibiting herbicide, whereby a formulation with 75% (w/w) of AHAS-inhibiting herbicide is obtained.

H. Gel-Formulation (GF). In an agitated ball mill, 20 parts by weight of the AHAS-inhibiting herbicide are comminuted with addition of 10 parts by weight of dispersants, 1 part by weight of a gelling agent wetters and 70 parts by weight of water or of an organic solvent to give a fine AHAS-inhibiting herbicide suspension. Dilution with water gives a stable suspension of the AHAS-inhibiting herbicide, whereby a formulation with 20% (w/w) of AHAS-inhibiting herbicide is obtained. This gel formulation is suitable for use as a seed treatment.

2. Products to be applied undiluted for foliar applications. For seed treatment purposes, such products may be applied to the seed diluted.

A. Dustable powders (DP, DS). Five parts by weight of the AHAS-inhibiting herbicide are ground finely and mixed intimately with 95 parts by weight of finely divided kaolin. This gives a dustable product having 5% (w/w) of AHAS-inhibiting herbicide.

B. Granules (GR, FG, GG, MG). One-half part by weight of the AHAS-inhibiting herbicide is ground finely and associated with 95.5 parts by weight of carriers, whereby a formulation with 0.5% (w/w) of AHAS-inhibiting herbicide is obtained. Current methods are extrusion, spray-drying or the fluidized bed. This gives granules to be applied undiluted for foliar use.

Conventional seed treatment formulations include, for example, flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds.

In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

For seed treatment, seeds of the rice plants of the present invention are treated with herbicides, preferably herbicides selected from the group consisting of AHAS-inhibiting herbicides, such as, amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid, pyrithiobac, and mixtures thereof, or with a formulation comprising an AHAS-inhibiting herbicide.

The term seed treatment comprises all suitable seed treatment techniques known in the art, such as, seed dressing, seed coating, seed dusting, seed soaking, and seed pelleting.

In accordance with one variant of the present invention, a further subject of the invention is a method of treating soil by the application, in particular into the seed drill: either of a granular formulation containing the AHAS-inhibiting herbicide as a composition/formulation (e.g., a granular formulation, with optionally one or more solid or liquid, agriculturally acceptable carriers and/or optionally with one or more agriculturally acceptable surfactants.

The present invention also comprises seeds coated with or containing with a seed treatment formulation comprising at least one AHAS-inhibiting herbicide selected from the group consisting of amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid, and pyrithiobac.

The term seed embraces seeds and plant propagules of all kinds including, but not limited to, true seeds, seed pieces, suckers, corms, bulbs, fruit, tubers, grains, cuttings, cut shoots and the like and means in a preferred embodiment true seeds.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

The seed treatment application with the AHAS-inhibiting herbicide or with a formulation comprising the AHAS-inhibiting herbicide is carried out by spraying or dusting the seeds before sowing of the plants and before emergence of the plants.

In the treatment of seeds, the corresponding formulations are applied by treating the seeds with an effective amount of the AHAS-inhibiting herbicide or a formulation comprising the AHAS-inhibiting herbicide. Herein, the application rates are generally from 0.1 g to 10 kg of the a.i. (or of the mixture of a.i. or of the formulation) per 100 kg of seed, preferably from 1 g to 5 kg per 100 kg of seed, in particular from 1 g to 2.5 kg per 100 kg of seed.

The present invention provides a method for combating undesired vegetation or controlling weeds comprising contacting the seeds of the rice plants according to the present invention before sowing and/or after pre-germination with an AHAS-inhibiting herbicide. The method can further comprise sowing the seeds, for example, in soil in a field or in a potting medium in greenhouse. The method finds particular use in combating undesired vegetation or controlling weeds in the immediate vicinity of the seed.

The control of undesired vegetation is understood as meaning the killing of weeds and/or otherwise retarding or inhibiting the normal growth of the weeds. Weeds, in the broadest sense, are understood as meaning all those plants which grow in locations where they are undesired.

The weeds may include, for example, dicotyledonous and monocotyledonous weeds. Dicotyledonous weeds include, but are not limited to, weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus*, and *Taraxacum*. Monocotyledonous weeds include, but are not limited to, weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus*, and *Apera*.

In addition, the weeds of the present invention can include, for example, crop plants that are growing in an undesired location. For example, a volunteer soybean plant that is in a field that predominantly comprises rice plants can be considered a weed, if the soybean plant is undesired in the field of rice plants. Another example of a weed of the present invention is red rice which is the same species as cultivated rice.

Transformation Techniques:

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years, several methods for producing transgenic plants have been developed, and the present invention, in particular embodiments, also relates to transformed versions of the claimed cultivar.

Culture for expressing desired structural genes and cultured cells are known in the art. Also as known in the art, rice is transformable and regenerable such that whole plants containing and expressing desired genes under regulatory control may be obtained. General descriptions of plant expression vectors and reporter genes and transformation protocols can be found in Gruber, et al., "Vectors for Plant Transformation", in *Methods in Plant Molecular Biology & Biotechnology* in Glich, et al., (Eds. pp. 89-119, CRC Press, 1993). Moreover GUS expression vectors and GUS gene cassettes are available from Clone Tech Laboratories, Inc., Palo Alto, Calif. while luciferase expression vectors and luciferase gene cassettes are available from Pro Mega Corp. (Madison, Wis.). General methods of culturing plant tissues are provided for example by Maki, et al., "Procedures for Introducing Foreign DNA into Plants" in *Methods in Plant Molecular Biology & Biotechnology*, Glich, et al., (Eds. pp. 67-88 CRC Press, 1993); and by Phillips, et al., "Cell-Tissue Culture and In-Vitro Manipulation" in *Corn & Corn Improvement*, 3rd Edition; Sprague, et al., (Eds. pp. 345-387 American Society of Agronomy Inc., 1988). Methods of introducing expression vectors into plant tissue include the direct infection or co-cultivation of plant cells with *Agrobacterium tumefaciens*, described for example by Horsch et al., *Science,* 227:1229 (1985). Descriptions of *Agrobacterium* vector systems and methods for *Agrobacterium*-mediated gene transfer are provided by Gruber, et al., supra.

Useful methods include but are not limited to expression vectors introduced into plant tissues using a direct gene transfer method such as microprojectile-mediated delivery, DNA injection, electroporation and the like. More preferably expression vectors are introduced into plant tissues using a microprojectile media delivery system with a biolistic device or using *Agrobacterium*-mediated transformation. Transformant plants obtained with the protoplasm of the invention are intended to be within the scope of this invention.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed rice plants, using transformation methods as described below to incorporate transgenes into the genetic material of the rice plant(s).

Expression Vectors for Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., *Proc. Natl. Acad. Sci. U.S.A.,* 80:4803 (1983). Another commonly used selectable marker gene is the hygromycin phosphotransferase gene which confers resistance to the antibiotic hygromycin. Vanden Elzen et al., *Plant Mol. Biol.,* 5:299 (1985).

Selectable marker genes for plant transformation not of bacterial origin include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant. Hayford et al., *Plant Physiol.* 86:1216 (1988); Jones et al., *Mol. Gen. Genet.,* 210:86 (1987); Svab et al., *Plant Mol. Biol.* 14:197 (1990); Hille et al., *Plant Mol. Biol.* 7:171 (1986). Other selectable marker genes confer resistance to herbicides such as glyphosate, glufosinate or bromoxynil. Comai et al., *Nature* 317:741-744 (1985), Gordon-Kamm et al., *Plant Cell* 2:603-618 (1990) and Stalker et al., *Science* 242:419-423 (1988).

Selectable marker genes for plant transformation not of bacterial origin include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS, β-galactosidase, luciferase and chloramphenicol acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984). Another approach to the identification of relatively rare transformation events has been use of a gene that encodes a dominant constitutive regulator of the *Zea mays* anthocyanin pigmentation pathway. Ludwig et al., *Science* 247:449 (1990).

In vivo methods for visualizing GUS activity that do not require destruction of plant tissue are available. Molecular Probes publication 2908, IMAGENE GREEN, p. 1-4 (1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263: 802 (1994). GFP and mutants of GFP may be used as screenable markers.

Expression Vectors for Transformation: Promoters

Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters—An inducible promoter is operably linked to a gene for expression in rice. Optionally, the inducible promoter is operably linked to a nucleotide sequence encoding a signal sequence which is operably linked to a gene for expression in rice. With an inducible promoter the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Meft et al., *PNAS* 90:4567-4571 (1993)); In2 gene from maize which responds to benzenesulfonamide herbicide safeners (Hershey et al., *Mol. Gen Genetics* 227:229-237 (1991) and Gatz et al., *Mol. Gen. Genetics* 243:32-38 (1994)) or Tet repressor from Tn10 (Gatz et al., *Mol. Gen. Genetics* 227: 229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., *Proc. Natl. Acad. Sci. U.S.A.* 88:0421 (1991)).

B. Constitutive Promoters—A constitutive promoter is operably linked to a gene for expression in rice or the constitutive promoter is operably linked to a nucleotide sequence encoding a signal sequence which is operably linked to a gene for expression in rice.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985)) and the promoters from such genes as rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genetics* 231:276-285 (1992) and Atanassova et al., *Plant Journal* 2 (3): 291-300 (1992)).

The ALS promoter, Xba1/Nco1 fragment 5' to the *Brassica napus* ALS3 structural gene (or a nucleotide sequence similarity to said Xba1/Nco1 fragment), represents a particularly useful constitutive promoter. See PCT application WO96/30530.

C. Tissue-specific or Tissue-preferred Promoters—A tissue-specific promoter is operably linked to a gene for expression in rice. Optionally, the tissue-specific promoter is operably linked to a nucleotide sequence encoding a signal sequence which is operably linked to a gene for expression in rice. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476-482 (1983) and Sengupta-Gopalan et al., *Proc. Natl. Acad. Sci. U.S.A.* 82:3320-3324 (1985)); a leaf-specific and light-induced promoter such as that from cab or rubisco (Simpson et al., *EMBO J.* 4(11): 2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992); Close, P. S., Master's Thesis, Iowa State University (1993); Knox, C., et al., *Plant Mol. Biol.* 9:3-17 (1987); Lerner et al., *Plant Physiol.* 91:124-129 (1989); Fontes et al., *Plant Cell* 3:483-496 (1991); Matsuoka et al., *Proc. Natl. Acad. Sci.* 88:834 (1991); Gould et al., *J. Cell. Biol.* 108:1657 (1989); Creissen et al., *Plant J.* 2:129 (1991); Kalderon, et al., *Cell* 39:499-509 (1984); Steifel, et al., *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

According to a preferred embodiment, the transgenic plant provided for commercial production of foreign protein is rice. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defences are often activated by specific interaction between the product of a disease resistance gene (R) in the plant and the product of a corresponding avirulence (Avr) gene in the pathogen. A plant cultivar can be transformed with cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al., *Cell* 78:1089 (1994) (*Arabidopsis* RSP2 gene for resistance to *Pseudomonas syringae*).

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

C. A lectin. See, for example, the disclosure by Van Damme et al., *Plant Molec. Biol.* 24:25 (1994), who disclose the nucleotide sequences of several *Clivia miniata* mannose-binding lectin genes.

D. A vitamin-binding protein such as avidin. See PCT application US93/06487. The application teaches the use of avidin and avidin homologues as larvicides against insect pests.

E. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyper-accumulation of a monoterpene, a sesquiterpene, a steroid, a hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect *Biochem. Molec. Biol.* 23:691 (1993), who teach the nucleotide sequence of a cDNA encoding tobacco hornworm chitinase, and Kawalleck et al., *Plant Molec. Biol.* 21:673 (1993), who provide the nucleotide sequence of the parsley ubi4-2 polyubiquitin gene.

K. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

L. A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., *Plant Sci* 89:43 (1993), of heterologous expression of a cecropin-β, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., *Nature* 366:469 (1993), who show that transgenic plants expressing recombinant antibody genes are protected from virus attack.

Q. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

R. A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance conferred by mutant 5-enolpyruvlshikimate-3-phosphate synthase (EPSP) and aroA genes, respectively) and other phosphono compounds such as glufosinate (phosphinothricin acetyl transferase (PAT) and *Streptomyces hygroscopicus* PAT, bar, genes), and pyridinoxy or phenoxy propionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., *Bio/Technology* 7:61 (1989), describe the production of transgenic plants that express chimeric bar genes coding for PAT activity. Exemplary of genes conferring resistance to phenoxy propionic acids and cyclohexones, such as sethoxydim and haloxyfop are the Accl-S1, Accl-S2 and Accl-S3 genes described by Marshall et al., *Theor. Appl. Genet.* 83:435 (1992).

C. An herbicide that inhibits photosynthesis, such as a triazine (psbA and gs+ genes) or a benzonitrile (nitrilase gene). Przibilla et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See Knultzon et al., *Proc. Natl. Acad. Sci. U.S.A.* 89:2624 (1992).

B. Decreased phytate content, 1) Introduction of a phytase-encoding gene would enhance breakdown of phytate, adding more free phosphate to the transformed plant. For example, see Van Hartingsveldt et al., *Gene* 127:87 (1993), for a disclosure of the nucleotide sequence of an *Aspergillus niger* phytase gene; 2) A gene could be introduced that reduced phytate content. In maize, this, for example, could be accomplished, by cloning and then reintroducing DNA associated with the single allele which is responsible for maize mutants characterized by low levels of phytic acid. See Raboy et al., *Maydica* 35:383 (1990).

C. Modified carbohydrate composition effected, for example, by transforming plants with a gene coding for an enzyme that alters the branching pattern of starch. See Shiroza et al., *J. Bacteol.* 170:810 (1988) (nucleotide sequence of *Streptococcus* mutants fructosyltransferase gene), Steinmetz et al., *Mol. Gen. Genet.* 20:220 (1985) (nucleotide sequence of *Bacillus subtilis* levansucrase gene), Pen et al., *Bio/Technology* 10:292 (1992) (production of transgenic plants that express *Bacillus lichenifonnis* α-amylase), Elliot et al., *Plant Molec. Biol.* 21:515 (1993) (nucleotide sequences of tomato invertase genes), Søgaard et al., *J. Biol. Chem.* 268:22480 (1993) (site-directed mutagenesis of barley α-amylase gene), and Fisher et al., *Plant Physiol.* 102:1045 (1993) (maize endosperm starch branching enzyme II).

Methods for Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89-119.

A. *Agrobacterium*-mediated Transformation—One method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 5,591,616 issued Jan. 7, 1997.

B. Direct Gene Transfer—Despite the fact the host range for *Agrobacterium*-mediated transformation is broad, some major cereal crop species and gymnosperms have generally been recalcitrant to this mode of gene transfer, even though some success has recently been achieved in rice and corn. Hiei et al., *The Plant Journal* 6:271-282 (1994) and U.S. Pat. No. 5,591,616 issued Jan. 7, 1997. Several methods of plant transformation collectively referred to as direct gene transfer, have been developed as an alternative to *Agrobacterium*-mediated transformation.

A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *Bio/Technology* 6:559-563 (1988), Sanford, J. C., *Physiol Plant* 7:206 (1990), Klein et al., *Biotechnology* 10:268 (1992). In corn, several target tissues can be bombarded with DNA-coated microprojectiles in order to produce transgenic plants, including, for example, callus (Type I or Type II), immature embryos, and meristematic tissue.

Another method for physical delivery of DNA to plants is sonication of target cells. Zhang et al., *Bio/Technology* 9:996 (1991). Additionally, liposome and spheroplast fusion have been used to introduce expression vectors into plants. Deshayes et al., *EMBO J.*, 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-ornithine has also been reported. Hain et al., *Mol.*

*Gen. Genet.* 199:161 (1985) and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4:1495-1505 (1992) and Spencer et al., *Plant Mol. Biol.* 24:51-61 (1994).

Following transformation of rice target tissues, expression of the above-described selectable marker genes allows for preferential selection of transformed cells, tissues and/or plants, using regeneration and selection methods now well known in the art.

The foregoing methods for transformation would typically be used for producing a transgenic cultivar. The transgenic cultivar could then be crossed, with another (non-transformed or transformed) cultivar, in order to produce a new transgenic cultivar. Alternatively, a genetic trait which has been engineered into a particular rice cultivar using the foregoing transformation techniques could be moved into another cultivar using traditional backcrossing techniques that are well known in the plant breeding arts. For example, a backcrossing approach could be used to move an engineered trait from a public, non-elite cultivar into an elite cultivar, or from a cultivar containing a foreign gene in its genome into a cultivar which does not contain that gene. As used herein, "crossing" can refer to a simple X by Y cross, or the process of backcrossing, depending on the context.

Single Gene Conversion

When the term rice plant is used in the context of the present invention, this also includes any single gene conversions of that cultivar. The term single gene converted plant as used herein refers to those rice plants which are developed by a plant breeding technique called backcrossing wherein essentially all of the desired morphological and physiological characteristics of a cultivar are recovered in addition to the single gene transferred into the cultivar via the backcrossing technique. Backcrossing methods can be used with the present invention to improve or introduce a characteristic into the cultivar. The term backcrossing as used herein refers to the repeated crossing of a hybrid progeny back to one of the parental rice plants, the recurrent parent, for that cultivar, i.e., backcrossing 1, 2, 3, 4, 5, 6, 7, 8, 9 or more times to the recurrent parent. The parental rice plant which contributes the gene for the desired characteristic is termed the nonrecurrent or donor parent. This terminology refers to the fact that the nonrecurrent parent is used one time in the backcross protocol and therefore does not recur. The parental rice plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original cultivar of interest (recurrent parent) is crossed to a second cultivar (nonrecurrent parent) that carries the single gene of interest to be transferred. The resulting progeny from this cross are then crossed again to the recurrent parent and the process is repeated until a rice plant is obtained wherein essentially all of the desired morphological and physiological characteristics of the recurrent parent are recovered in the converted plant, in addition to the single transferred gene from the nonrecurrent parent as determined at the 5% significance level when grown in the same environmental conditions.

The selection of a suitable recurrent parent is an important step for a successful backcrossing procedure. The goal of a backcross protocol is to alter or substitute a single trait or characteristic in the original cultivar. To accomplish this, a single gene of the recurrent cultivar is modified or substituted with the desired gene from the nonrecurrent parent, while retaining essentially all of the rest of the desired genetic, and therefore the desired physiological and morphological, constitution of the original cultivar. The choice of the particular nonrecurrent parent will depend on the purpose of the backcross; one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new cultivar but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

Tissue Culture

Further reproduction of the variety can occur by tissue culture and regeneration. Tissue culture of various tissues of rice and regeneration of plants therefrom is well known and widely published. For example, reference may be had to Komatsuda, T. et al., Crop Sci. 31:333-337 (1991); Stephens, P. A., et al., *Theor. Appl. Genet.* (1991) 82:633-635; Komatsuda, T. et al., *Plant Cell, Tissue and Organ Culture,* 28:103-113 (1992); Dhir, S. et al., *Plant Cell Reports* (1992) 11:285-289; Pandey, P. et al., *Japan J. Breed.* 42:1-5 (1992); and Shetty, K., et al., *Plant Science* 81:245-251 (1992); as well as U.S. Pat. No. 5,024,944 issued Jun. 18, 1991 to Collins et al., and U.S. Pat. No. 5,008,200 issued Apr. 16, 1991 to Ranch et al. Thus, another aspect of this invention is to provide cells which upon growth and differentiation produce rice plants having the physiological and morphological characteristics of rice variety CL172.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, anthers, and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

As used herein, the term "plant" includes plant cells, plant protoplasts, plant cells of tissue culture from which rice plants can be regenerated, plant calli, plant clumps, and plant cells that are intact in plants or parts of plants, such as pollen, flowers, embryos, ovules, seeds, pods, leaves, stems, pistils, anthers and the like. Thus, another aspect of this invention is to provide for cells which upon growth and differentiation produce a cultivar having essentially all of the physiological and morphological characteristics of CL172.

The present invention contemplates a rice plant regenerated from a tissue culture of a variety (e.g., CL172) or hybrid plant of the present invention. As is well known in the art, tissue culture of rice can be used for the in vitro regeneration of a rice plant. Tissue culture of various tissues of rice and regeneration of plants therefrom is well known and widely published. For example, reference may be had to Chu, Q. R., et al., (1999) "Use of bridging parents with high anther culturability to improve plant regeneration and breeding value in rice", *Rice Biotechnology Quarterly* 38:25-26; Chu, Q. R., et al., (1998), "A novel plant regeneration medium for rice anther culture of Southern U.S. crosses", *Rice Biotechnology Quarterly* 35:15-16; Chu, Q. R., et al., (1997), "A novel basal medium for embryogenic callus induction of Southern US crosses", *Rice Biotechnology Quarterly* 32:19-20; and Oono, K., "Broadening the Genetic Variability By Tissue Culture Methods", *Jap. J. Breed.* 33 (Suppl. 2), 306-307, illus. 1983. Thus, another aspect of this invention is to provide cells which upon growth and differentiation produce rice plants having the physiological and morphological characteristics of variety CL172.

Duncan, et al., *Planta* 165:322-332 (1985) reflects that 97% of the plants cultured that produced callus were capable of plant regeneration. Subsequent experiments with both cultivars and hybrids produced 91% regenerable callus that produced plants. In a further study in 1988, Songstad, et al., *Plant Cell Reports* 7:262-265 (1988), reports several media additions that enhance regenerability of callus of two cultivars. Other published reports also indicated that "non-traditional" tissues are capable of producing somatic embryogenesis and plant regeneration. K. P. Rao et al., *Maize Genetics Cooperation Newsletter*, 60:64-65 (1986), refers to somatic embryogenesis from glume callus cultures and B. V. Conger, et al., *Plant Cell Reports*, 6:345-347 (1987) indicates somatic embryogenesis from the tissue cultures of corn leaf segments. Thus, it is clear from the literature that the state of the art is such that these methods of obtaining plants are routinely used and have a very high rate of success. Thus, another aspect of this invention is to provide cells which upon growth and differentiation produce rice plants having the physiological and morphological characteristics of rice cultivar CL172.

The utility of rice cultivar CL172 also extends to crosses with other species. Commonly, suitable species will be of the family Graminaceae, and especially of the genera *Zea, Tripsacum, Croix, Schlerachne, Polytoca, Chionachne*, and *Trilobachne*, of the tribe Maydeae.

Additional Breeding Methods

Although specific breeding objectives vary somewhat in the different regions, increasing yield is a primary objective in all programs. Grain yield of rice is determined by the number of panicles per unit area, the number of fertile florets per panicle, and grain weight per floret. Increases in any or all of these yield components may provide a mechanism to obtain higher yields. Heritable variation exists for all of these components, and breeders may directly or indirectly select for increases in any of them.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to low temperatures, and better grain quality including improve physical appearance, cooking and taste characteristics, and milling yield (% whole kernel milled rice or head rice and % total milled rice).

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection, or a combination of these methods.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from 8 to 12 years from the time the first cross is made and may rely on the development of improved breeding lines as precursors. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of rice plant breeding is to develop new, unique and superior rice cultivars and hybrids. The breeder initially selects and crosses two or more parental lines, followed by self-pollination and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same rice traits.

Each year, the plant breeder selects the germplasm to advance to the next generation. This germplasm is grown under unique and different geographical, climatic and soil conditions and further selections are then made, during and at the end of the growing season. The cultivars which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new rice cultivars.

The development of new rice cultivars requires the development and selection of rice varieties, the crossing of these varieties and selection of superior hybrid crosses. The hybrid seed is produced by manual crosses between selected male-fertile parents or by using male sterility systems. These hybrids are selected for certain single gene traits such as semi-dwarf plant type, pubescence, awns, and apiculus color which indicate that the seed is truly a hybrid. Additional data on parental lines, as well as the phenotype of the hybrid, influence the breeder's decision whether to continue with the specific hybrid cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents which possess favorable, complementary traits are crossed to produce an $F_1$. An $F_2$ population is produced by selfing one or several $F_1$'s. Selection of the best individuals may begin with evaluation of $F_1$ plants, continue with selection of $F_2$ plants, and on in the $F_3$, where the best individuals in the best families are selected and advanced. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, rice breeders commonly harvest one or more seeds from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh panicles with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., Allard, 1960; Simmonds, 1979; Sneep et al., 1979; Fehr, 1987; Marshall and Wadsworth, 1994; Champagne, 2004).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

This invention also is directed to methods for producing a rice plant by crossing a first parent rice plant with a second parent rice plant wherein the first or second parent rice plant is a rice plant of the variety CL172. Further, both first and second parent rice plants can come from the rice variety CL172. Thus, any such methods using the rice variety CL172 are part of this invention: selfing, backcrosses, hybrid production, crosses to populations, and the like. All plants produced using rice variety CL172 as a parent are within the scope of this invention, including those developed from varieties derived from rice variety CL172. Advantageously, the rice variety could be used in crosses with other, different, rice plants to produce the first generation ($F_1$) rice hybrid seeds and plants with superior characteristics. The variety of the invention can also be used for transformation where exogenous genes are introduced and expressed by the variety of the invention. Genetic variants created either through traditional breeding methods using variety CL172 or through transformation of CL172 by any of a number of protocols known to those of skill in the art are intended to be within the scope of this invention.

The following describes breeding methods that may be used with cultivar CL172 in the development of further rice plants. One such embodiment is a method for developing an CL172 progeny rice plant in a rice plant breeding program comprising: obtaining the rice plant, or a part thereof, of cultivar CL172 utilizing said plant or plant part as a source of breeding material and selecting an CL172 progeny plant with molecular markers in common with CL172 and/or with morphological and/or physiological characteristics selected from the characteristics listed in Tables 1 through 14. Breeding steps that may be used in the rice plant breeding program include pedigree breeding, back crossing, mutation breeding, and recurrent selection. In conjunction with these steps, techniques such as RFLP-enhanced selection, genetic marker enhanced selection (for example SSR markers) and the making of double haploids may be utilized.

Another method involves producing a population of cultivar CL172 progeny rice plants, comprising crossing cultivar CL172 with another rice plant, thereby producing a population of rice plants, which, on average, derive 50% of their alleles from cultivar CL172. A plant of this population may be selected and repeatedly selfed or sibbed with a rice cultivar resulting from these successive filial generations. One embodiment of this invention is the rice cultivar produced by this method and that has obtained at least 50% of its alleles from cultivar CL172.

One of ordinary skill in the art of plant breeding would know how to evaluate the traits of two plant varieties to determine if there is no significant difference between the two traits expressed by those varieties. For example, see Fehr and Walt, Principles of Cultivar Development, p 261-286 (1987). Thus the invention includes rice cultivar CL172 progeny rice plants comprising a combination of at least two CL172 traits selected from the group consisting of those listed in Tables 1-14 or the CL172 combination of traits listed in the Summary of the Invention, so that said progeny rice plant is not significantly different for said traits than rice cultivar CL172 as determined at the 5% significance level when grown in the same environment. Using techniques described herein, molecular markers may be used to identify said progeny plant as a CL172 progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of cultivar CL172 may also be characterized through their filial relationship with rice cultivar CL172, as for example, being within a certain number of breeding crosses of rice cultivar CL172. A breeding cross is a cross made to introduce new genetics into the progeny, and is distinguished from a cross, such as a self or a sib cross, made to select among existing genetic alleles. The lower the number of breeding crosses in the pedigree, the closer the relationship between rice cultivar CL172 and its progeny. For example, progeny produced by the methods described herein may be within 1, 2, 3, 4, 5, 6 or 7 breeding crosses of rice cultivar CL172.

The seed of rice cultivar CL172, the plant produced from the cultivar seed, the hybrid rice plant produced from the crossing of the cultivar, hybrid seed, and various parts of the hybrid rice plant and transgenic versions of the foregoing, can be utilized for human food, livestock feed, and as a raw material in industry.

Tables

In Table 2, agronomic characteristics are shown for rice cultivar CL172 and for fourteen other rice cultivars. These data are the result of the Arkansas Rice Performance Trials (ARPT) conducted in 2012. (Stuttgart, Rice Research and Extension Center (RREC); Keiser, Northeast Research and Extension Center (NEREC); Clay County Farmer Field, (CC), Corning, Ark.; Newport Extension Center (NEC, NPBS); Pine Tree (PTRS)). Column one shows the variety, column two shows the average grain yield in bushels per acre, column three shows the average plant height in inches, column four shows the maturity in days at 50% heading, column five shows the average percent lodging, column six shows the average test weight in pounds, column seven shows the overall rank and column eight shows the milling figures of percent head rice (or whole kernel rice) as compared to the percent of total milled rice (HR-TR).

TABLE 2

| Variety | Grain yield (bu/ac) | Plant Height (in) | 50% Heading | Lodging | Test Weight (lbs) | Overall Rank | HR-TR |
| --- | --- | --- | --- | --- | --- | --- | --- |
| CL172 | 215 | 38 | 85 | 0 | 43 | 17 | 62-71 |
| CL111 | 180 | 39 | 82 | 35 | 42 | 82 | 62-71 |
| CL142-AR | 193 | 44 | 85 | 46 | 43 | 61 | 51-70 |
| CL151 | 204 | 39 | 84 | 23 | 42 | 40 | 63-71 |
| CL152 | 192 | 38 | 84 | 31 | 42 | 65 | 63-71 |
| CL162 | 186 | 42 | 82 | 38 | 41 | 72 | 59-70 |
| CL181-AR | 195 | 35 | 86 | 1 | 43 | 59 | 61-70 |
| CL261 | 180 | 39 | 83 | 31 | 43 | 81 | 59-69 |
| CL XL729 | 203 | 43 | 84 | 42 | 41 | 42 | 59-70 |
| CL XL745 | 205 | 43 | 80 | 47 | 41 | 37 | 57-72 |
| CL XP751 | 246 | 37 | 75 | 19 | 42 | 1 | 50-70 |
| LaKast | 210 | 43 | 83 | 48 | 42 | 28 | 61-72 |
| Francis | 213 | 41 | 86 | 45 | 43 | 19 | 63-72 |
| Roy J | 234 | 41 | 89 | 3 | 42 | 3 | 64-72 |
| Wells | 205 | 40 | 85 | 36 | 43 | 38 | 54-71 |

In Table 3, agronomic characteristics are shown for rice cultivar CL172 and for twelve other rice cultivars. These data are the result of the Arkansas Rice Performance Trials (ARPT) conducted in 2013. (Stuttgart, Rice Research and Extension Center (RREC); Keiser, Northeast Research and Extension Center (NEREC); Clay County Farmer Field, (CC), Corning, Ark.; Desha County Farmer Field (DESHA); Newport Extension Center (NEC); Pine Tree (PTRS)). Column one shows the variety, column two shows the average grain yield in bushels per acre, column three shows the average plant height in inches, column four shows the maturity in days at 50% heading, column five shows the average percent lodging, column six shows the average test weight in pounds, column seven shows the overall rank and column eight shows the milling figures of percent head rice (or whole kernel rice) as compared to the percent of total milled rice (HR-TR).

TABLE 3

| Variety | Grain yield (bu/ac) | Plant Height (in) | 50% Heading | Lodging | Test Weight (lbs) | Overall Rank | HR-TR |
|---|---|---|---|---|---|---|---|
| CL172 | 186 | 36 | 80 | 0 | 41 | 55 | 65-69 |
| CL111 | 175 | 39 | 77 | 0 | 41 | 69 | 62-69 |
| CL142AR | 186 | 45 | 80 | 0 | 41 | 56 | 59-69 |
| CL151 | 180 | 39 | 79 | 0 | 40 | 64 | 64-69 |
| CL152 | 160 | 38 | 81 | 0 | 41 | 85 | 65-69 |
| CL162 | 170 | 41 | 78 | 2 | 41 | 77 | 61-68 |
| RT CL L729 | 199 | 42 | 79 | 28 | 41 | 16 | 60-68 |
| RT CL L745 | 176 | 44 | 77 | 30 | 41 | 67 | 60-69 |
| LaKast | 197 | 42 | 79 | 0 | 41 | 20 | 61-69 |
| Francis | 196 | 40 | 81 | 0 | 41 | 26 | 65-70 |
| Mermentau | 183 | 36 | 79 | 0 | 41 | 60 | 64-69 |
| Roy J | 203 | 42 | 85 | 0 | 40 | 7 | 63-69 |
| Wells | 191 | 41 | 81 | 0 | 41 | 40 | 61-69 |

In Table 4, agronomic characteristics are shown for rice cultivar CL172 and for eleven other rice cultivars. These data are the mean of the Arkansas Rice Performance Trials (ARPT) conducted in 2012-2013. (Stuttgart, Rice Research and Extension Center (RREC); Keiser, Northeast Research and Extension Center (NEREC); Clay County Farmer Field, (CC), Corning, Ark.; Desha County Farmer Field (DESHA); Newport Extension Center (NEC); Pine Tree (PTRS)). Column one shows the variety, column two shows the average grain yield in bushels per acre, column three shows the average plant height in inches, column four shows the maturity in days at 50% heading and column five shows the milling figures of percent head rice (or whole kernel rice) as compared to the percent of total milled rice (HR-TR).

TABLE 4

| Variety | Grain yield (bu/ac) | Plant Height (in) | 50% Heading | HR-TR |
|---|---|---|---|---|
| CL172 | 201 | 37 | 83 | 64-71 |
| CL111 | 178 | 39 | 80 | 63-70 |
| CL142AR | 190 | 45 | 83 | 56-70 |
| CL151 | 192 | 39 | 82 | 64-71 |
| CL152 | 176 | 38 | 83 | 65-71 |
| CL162 | 178 | 41 | 80 | 61-70 |
| RT CL XL729 | 201 | 43 | 82 | 61-70 |
| RT CL XL745 | 191 | 44 | 79 | 59-71 |
| Roy J | 219 | 42 | 87 | 64-71 |
| Francis | 205 | 41 | 84 | 65-72 |
| Wells | 198 | 41 | 83 | 58-71 |
| LaKast | 204 | 43 | 81 | 62-71 |

In Table 5, agronomic characteristics are shown for rice cultivar CL172 and fourteen other rice cultivars. The data are the result of trials at the Arkansas Rice Performance Trials (ARPT) from 2012 by location, including Clay County Farmer Field, (CC), Corning, Ark.; Northeast Research and Extension Center, (NEREC), Keiser, Ark.; Newport Extension Center, (NEC), Newport, Ark.; Pine Tree Research Station, (PTRS), Colt, Ark.; and Rice Research and Extension Center, (RREC), Stuttgart, Ark. Column one shows the variety, columns two to six give the average grain yield for each of 5 different locations for each variety in bushels per acre, column seven shows the mean yield for the 5 locations in bushels per acre, columns eight to twelve show the average head rice (%) to total rice (%) ratio for each of 5 different locations and column thirteen shows the mean head rice (%) to total rice (%) ratio for the 5 locations.

TABLE 5

| Variety | Grain yield (bu/ac) | | | | | | Head rice (%)-Total rice (%) | | | | | |
|---|---|---|---|---|---|---|---|---|---|---|---|---|
| | CC | NEREC | NEC | PTRS | RREC | Mean | CC | NEREC | NEC | PTRS | RREC | Mean |
| CL172 | 219 | 227 | 159 | 205 | 262 | 215 | 65-71 | 62-72 | 61-71 | 60-69 | 63-71 | 62-71 |
| CL111 | 221 | 180 | 161 | 165 | 170 | 180 | 65-72 | 64-71 | 60-70 | 57-69 | 66-72 | 62-71 |
| CL142AR | 244 | 216 | 117 | 211 | 179 | 193 | 49-71 | 55-72 | 48-70 | 48-69 | 54-71 | 51-71 |
| CL151 | 224 | 234 | 207 | 188 | 169 | 204 | 64-71 | 61-70 | 67-72 | 59-70 | 66-71 | 63-71 |
| CL152 | 227 | 194 | 159 | 207 | 171 | 192 | 61-71 | 63-72 | 66-71 | 60-70 | 65-71 | 63-71 |
| CL162 | 177 | 201 | | 178 | 190 | 186 | 61-71 | 58-70 | | 55-69 | 64-71 | 60-70 |
| CL181AR | 213 | 212 | 139 | 211 | 200 | 195 | 62-70 | 63-72 | 61-69 | 61-70 | 57-70 | 61-70 |
| CL261 | 170 | 209 | 192 | 156 | 172 | 180 | 61-70 | 59-70 | 58-60 | 55-67 | 63-70 | 59-67 |
| CLXL729 | 253 | 191 | 196 | 183 | 193 | 203 | 60-71 | 60-71 | 59-70 | 57-69 | 61-71 | 59-70 |
| CLXL745 | 252 | 164 | | 198 | 206 | 205 | 59-72 | 56-71 | | 52-71 | 62-72 | 57-72 |
| CLXP751 | 261 | 226 | 205 | 262 | 274 | 246 | 49-70 | 43-69 | 55-69 | 40-69 | 64-71 | 50-70 |
| Francis | 219 | 227 | 192 | 215 | | 213 | 62-72 | 61-72 | 67-72 | 61-72 | 64-72 | 63-72 |
| LaKast | 227 | 215 | 210 | 207 | 193 | 210 | 58-72 | 62-72 | 63-73 | 56-70 | 65-72 | 61-72 |
| RoyJ | 222 | 212 | 217 | 260 | 257 | 234 | 63-72 | 68-73 | 66-71 | 60-72 | 61-73 | 64-72 |
| Wells | 221 | 204 | 155 | 228 | 215 | 205 | 60-72 | 55-72 | 49-71 | 51-71 | 54-71 | 54-71 |

In Table 6, agronomic characteristics are shown for rice cultivar CL172 and twelve other rice cultivars. The data are the result of trials at the Arkansas Rice Performance Trials (ARPT) from 2013 by location, including Clay County Farmer Field, (CLAY), Corning, Ark.; Desha County Farmer Field (DESHA), Northeast Research and Extension Center, (NEREC), Keiser, Ark.; Newport Extension Center, (NEC), Newport, Ark.; Pine Tree Research Station, (PTRS), Colt, Ark.; and Rice Research and Extension Center, (RREC), Stuttgart, Ark. Column one shows the variety, columns two to seven give the average grain yield for each of 6 different locations for each variety in bushels per acre, column eight shows the mean yield for the 6 locations in bushels per acre, columns nine to fourteen show the average head rice (%) to total rice (%) ratio for each of 6 different locations and column fifteen shows the mean head rice (%) to total rice (%) ratio for the 6 locations.

TABLE 6

| Variety | Grain yield (bu/ac) | | | | | | | Head rice (%)-Total rice (%) | | | | | | |
|---|---|---|---|---|---|---|---|---|---|---|---|---|---|---|
| | CLAY | DESHA | NEREC | NEC | PTRS | RREC | Mean | CLAY | DESHA | NEREC | NEC | PTRS | RREC | Mean |
| CL172 | 170 | 232 | 159 | 161 | 178 | 217 | 186 | 68-71 | 65-69 | 68-71 | 65-70 | 63-68 | 65-70 | 66-70 |
| CL111 | 161 | 206 | 148 | 158 | 187 | 190 | 175 | 65-69 | 63-69 | 67-71 | 68-71 | 63-69 | 58-68 | 64-69 |
| CL142-AR | 170 | 220 | 170 | 148 | 191 | 217 | 186 | 67-71 | 60-69 | 63-71 | 61-70 | 60-68 | 49-68 | 60-69 |
| CL151 | 190 | 134 | 192 | 133 | 209 | 222 | 180 | 67-70 | 63-69 | 68-71 | 66-70 | 63-68 | 62-69 | 65-70 |
| CL152 | 151 | 201 | 142 | 115 | 164 | 184 | 160 | 67-70 | 64-68 | 68-71 | 68-71 | 63-67 | 66-71 | 66-70 |
| CL162 | 154 | 194 | 170 | 132 | 177 | 192 | 170 | 66-70 | 62-68 | 65-70 | 64-70 | 60-67 | 55-67 | 62-69 |
| RT CL XL729 | 178 | 156 | 205 | 167 | 237 | 251 | 199 | 66-70 | 60-68 | 64-70 | 65-70 | 59-67 | 56-68 | 62-69 |
| RT CL XL745 | 156 | 177 | 143 | 162 | 217 | 202 | 176 | 66-71 | 62-70 | 62-71 | 65-71 | 57-67 | 54-67 | 61-69 |
| LaKast | 184 | 230 | 184 | 167 | 186 | 233 | 197 | 65-70 | 64-70 | 68-71 | 66-71 | 58-66 | 59-69 | 63-70 |
| Francis | 202 | 221 | 193 | 148 | 179 | 231 | 196 | 69-72 | 65-70 | 69-72 | 65-71 | 63-68 | 64-70 | 66-71 |
| Mermentau | 186 | 220 | 166 | 146 | 175 | 205 | 183 | 66-69 | 64-68 | 68-71 | 67-71 | 63-67 | 64-70 | 65-69 |
| Roy J | 200 | 231 | 204 | 169 | 182 | 233 | 203 | 65-70 | 64-70 | 68-72 | 61-70 | 60-67 | 63-70 | 63-70 |
| Wells | 198 | 221 | 175 | 165 | 174 | 213 | 191 | 66-70 | 63-70 | 63-72 | 63-70 | 59-67 | 57-69 | 62-70 |

In Table 7, agronomic characteristics are shown for rice cultivar CL172 and ten other rice cultivars. The data are the result of trials at the Cooperative Uniform Regional Rice Nursery (URRN) from 2012 for five locations, including Stuttgart, Ark.; Crowley, La.; Stoneville, Miss.; Campbell, Mo.; and Beaumont, Tex. Column one shows the variety, columns two to four give the yield for each of 3 different locations for each variety in pounds per acre, column five shows the average yield for the 3 locations in pounds per acre, columns six to ten show the number of days to 50% heading for each of 5 locations, column eleven shows the average number of days to 50% heading for the 5 locations, columns twelve to sixteen shows the height in centimeters for each of 5 different locations, column seventeen shows the average height in centimeters for the 5 locations, columns eighteen to twenty-two show the percent lodging for each of 5 different locations and column twenty-three shows the average percent lodging for the 5 locations. The MO yields were missing and TX also had low yields with many missing data. In MO, 10% lodging equals 0% lodging and everything is rated at least 10%.

TABLE 7

| Variety | Yield (lbs/ac) | | | | Days to 50% heading | | | | | | Height (cm) | | |
|---|---|---|---|---|---|---|---|---|---|---|---|---|---|
| | AR | LA | MS | Avg. | AR | LA | MO | MS | TX | Avg. | AR | LA | MO |
| CL172 | 8097 | 8511 | 10090 | 8899 | 96 | 84 | 92 | 79 | 82 | 87 | 85 | 90 | 91 |
| CL111 | 10155 | 8258 | 10326 | 9580 | 94 | 84 | 89 | 75 | . | 85 | 102 | 93 | 100 |
| CL151 | 11652 | 3506 | 10671 | 8610 | 94 | 85 | 91 | 77 | . | 87 | 105 | 96 | 99 |
| CL162 | 10289 | 1011 | 9375 | 6892 | 91 | 82 | 87 | 74 | 80 | 83 | 112 | 98 | 100 |
| CL181AR | 9394 | 6201 | 9522 | 8372 | 94 | 85 | 94 | 79 | 85 | 87 | 93 | 93 | 98 |
| CL142AR | 8959 | 3870 | 10419 | 7749 | 96 | 86 | 93 | 77 | 85 | 87 | 106 | . | 100 |
| CL152 | 10086 | 3289 | 9490 | 7622 | 96 | 86 | 92 | 78 | 81 | 86 | 103 | 88 | 97 |
| Roy J | 11325 | 4811 | 9853 | 8663 | 99 | 89 | 93 | 83 | 87 | 90 | 107 | 100 | 94 |
| Francis | 11989 | 3917 | 10195 | 8700 | 94 | 85 | 91 | 78 | 84 | 86 | 108 | 106 | 102 |
| Wells | 10428 | 5237 | 9986 | 8551 | 95 | 87 | 92 | 78 | 86 | 87 | 108 | 101 | 102 |
| RU0801081 | 11229 | 6923 | 10868 | 9673 | 94 | 83 | 91 | 76 | . | 86 | 113 | 106 | 98 |

TABLE 7-continued

| | Height (cm) | | | % Lodging | | | | | |
|---|---|---|---|---|---|---|---|---|---|
| Variety | MS | TX | Avg. | AR | LA | MO | MS | TX | Avg. |
| CL172 | . | 84 | 87 | 0 | 0 | 10 | 0 | 0 | 2 |
| CL111 | . | . | 98 | 13 | 0 | 90 | 0 | . | 26 |
| CL151 | . | . | 100 | 23 | 0 | 90 | 0 | . | 28 |
| CL162 | 112 | 102 | 105 | 23 | 0 | 90 | 0 | 0 | 23 |
| CL181AR | . | 92 | 94 | 0 | 0 | 70 | 0 | 0 | 14 |
| CL142AR | . | 110 | 105 | 0 | 0 | 90 | 0 | 0 | 18 |
| CL152 | 105 | 83 | 95 | 0 | 0 | 50 | 0 | 0 | 10 |
| Roy J | 105 | 110 | 103 | 0 | 0 | 90 | 0 | 0 | 18 |
| Francis | 102 | 104 | 104 | 3 | 0 | 80 | 0 | 0 | 17 |
| Wells | 107 | 111 | 106 | 0 | 0 | 60 | 0 | 0 | 12 |
| RU0801081 | . | . | 106 | 0 | 23 | 80 | 0 | . | 26 |

In Table 8, agronomic characteristics are shown for rice cultivar CL172 and ten other rice cultivars. The data are the result of trials at the Cooperative Uniform Regional Rice Nursery (URRN) from 2013 for five locations, including Stuttgart, Ark.; Crowley, La.; Stoneville, Miss.; Campbell, Mo.; and Beaumont, Tex. Column one shows the variety, columns two to six give the yield for each of 5 different locations for each variety in pounds per acre, column seven shows the average yield for the 5 locations in pounds per acre, columns eight to twelve show the number of days to 50% heading for each of 5 locations, column thirteen shows the average number of days to 50% heading for the 5 locations, columns fourteen to eighteen shows the height in centimeters for each of 5 different locations, column nineteen shows the average height in centimeters for the 5 locations, columns twenty to twenty-four show the percent lodging for each of 5 different locations and column twenty-five shows the average percent lodging for the 5 locations. In MO, 10% lodging equals 0% lodging and everything is rated at least 10%.

TABLE 8

| | Yield (lbs/ac) | | | | | | Days to 50% heading | | | | | |
|---|---|---|---|---|---|---|---|---|---|---|---|---|
| Variety | AR | LA | MO | MS | TX | Avg. | AR | LA | MO | MS | TX | Avg. |
| CL172 | 10031 | 9196 | 8975 | 5642 | 10450 | 8859 | 81 | 90 | 96 | 82 | 89 | 88 |
| CL 111 | 9744 | 11211 | 7052 | 7392 | 7815 | 8643 | 81 | 88 | 94 | 80 | 88 | 86 |
| CL 151 | 10810 | 11972 | 9783 | 8294 | 9482 | 10068 | 81 | 91 | 96 | 81 | 93 | 88 |
| CL162 | 9356 | 10024 | 6738 | 7519 | 9433 | 8614 | 81 | 90 | 92 | 80 | 84 | 85 |
| CL 181 AR | 9675 | 9285 | 9041 | 4434 | 9855 | 8458 | 82 | 93 | 95 | 82 | 92 | 89 |
| CL 142 AR | 10198 | 10032 | 10098 | 7987 | 10713 | 9805 | 83 | 93 | 89 | 83 | 85 | 87 |
| CL 152 | 9983 | 9257 | 8171 | 6976 | 9315 | 8740 | 83 | 94 | 90 | 82 | 89 | 88 |
| Roy J | 10801 | 9356 | 10176 | 8198 | 9772 | 9661 | 87 | 96 | 102 | 87 | 93 | 93 |
| Francis | 9744 | 8635 | 7868 | 7900 | 9835 | 8796 | 83 | 92 | 98 | 81 | 89 | 89 |
| Wells | 10219 | 8701 | 8934 | 8011 | 8916 | 8956 | 84 | 93 | 99 | 84 | 89 | 90 |
| RU0801081 | 10864 | 9414 | 10035 | 8838 | 9957 | 9822 | 80 | 88 | 93 | 81 | 91 | 86 |

| | Height (cm) | | | | | | % Lodging | | | | | |
|---|---|---|---|---|---|---|---|---|---|---|---|---|
| Variety | AR | LA | MO | MS | TX | Avg. | AR | LA | MO | MS | TX | Avg. |
| CL172 | 100 | 91 | 91 | 93 | 86 | 92 | 0 | 0 | 10 | 0 | 0 | 2 |
| CL 111 | 107 | 103 | 105 | 88 | 96 | 100 | 0 | 0 | 10 | 0 | 0 | 2 |
| CL 151 | 103 | 99 | 102 | 93 | 97 | 99 | 0 | 0 | 10 | 0 | 0 | 2 |
| CL162 | 118 | 107 | 107 | 106 | 98 | 107 | 0 | 0 | 10 | 0 | 0 | 2 |
| CL 181 AR | 97 | 87 | 89 | 90 | 87 | 90 | 0 | 0 | 10 | 0 | 0 | 2 |
| CL 142 AR | 122 | 111 | 110 | 116 | 107 | 113 | 0 | 0 | 10 | 0 | 0 | 2 |
| CL 152 | 99 | 97 | 100 | 99 | 94 | 98 | 0 | 0 | 10 | 0 | 0 | 2 |
| Roy J | 111 | 107 | 104 | 109 | 106 | 108 | 0 | 0 | 10 | 0 | 0 | 2 |
| Francis | 109 | 98 | 100 | 103 | 95 | 101 | 0 | 0 | 10 | 0 | 0 | 2 |
| Wells | 114 | 103 | 100 | 102 | 102 | 104 | 0 | 0 | 10 | 0 | 0 | 2 |
| RU0801081 | 112 | 99 | 100 | 102 | 109 | 105 | 0 | 0 | 10 | 0 | 0 | 2 |

Table 9 shows milling characteristics for rice cultivar CL172 and ten other rice cultivars. The data are the result of trials at the Cooperative Uniform Regional Rice Nursery (URRN) from 2012 for five locations, including Stuttgart, Ark.; Crowley, La.; Stoneville, Miss.; Campbell, Mo.; and Beaumont, Tex. Column one shows the variety, columns two to six give the percent head rice for each of 5 different locations for each variety, column seven shows the average percent head rice for the 5 locations, columns eight to twelve show the percent total rice for each of the 5 locations, column thirteen shows the average percent total rice for the 5 locations.

TABLE 9

| | % Head rice | | | | | | % Total rice | | | | | |
|---|---|---|---|---|---|---|---|---|---|---|---|---|
| Variety | AR | LA | MO | MS | TX | Avg. | AR | LA | MO | MS | TX | Avg. |
| CL172 | 58 | 52 | 62 | 57 | 55 | 57 | 71 | 69 | 67 | 66 | 68 | 68 |
| CL111 | 64 | 61 | 66 | 55 | . | 62 | 71 | 69 | 71 | 70 | . | 70 |
| CL151 | 64 | 52 | 66 | 57 | . | 60 | 71 | 69 | 70 | 70 | . | 70 |
| CL162 | 58 | 48 | 65 | 51 | 57 | 56 | 71 | 67 | 70 | 69 | 68 | 69 |
| CL181AR | 54 | 63 | 68 | 54 | 57 | 59 | 70 | 71 | 70 | 68 | 68 | 69 |
| CL142AR | 51 | 58 | 59 | 48 | 50 | 53 | 70 | 69 | 66 | 66 | 68 | 68 |
| CL152 | 65 | . | 61 | 53 | 47 | 57 | 70 | | 67 | 67 | 72 | 69 |
| Roy J | 60 | 52 | 60 | 54 | 47 | 54 | 70 | 70 | 65 | 70 | 69 | 69 |
| Francis | 58 | 61 | 70 | 53 | 54 | 59 | 71 | 70 | 73 | 71 | 67 | 70 |
| Wells | 53 | 64 | 67 | 49 | 53 | 57 | 71 | 71 | 71 | 71 | 67 | 70 |
| RU0801081 | 58 | 66 | 63 | 50 | . | 59 | 70 | 70 | 68 | 69 | . | 69 |

Table 10 shows milling characteristics for rice cultivar CL172 and ten other rice cultivars. The data are the result of trials at the Cooperative Uniform Regional Rice Nursery (URRN) from 2013 for five locations, including Stuttgart, Ark.; Crowley, La.; Stoneville, Miss.; Campbell, Mo.; and Beaumont, Tex. Column one shows the variety, columns two to six give the percent head rice for each of 5 different locations for each variety, column seven shows the average percent head rice for the 5 locations, columns eight to twelve show the percent total rice for each of the 5 locations, column thirteen shows the average percent total rice for the 5 locations.

TABLE 10

| | % Head rice | | | | | | % Total rice | | | | | |
|---|---|---|---|---|---|---|---|---|---|---|---|---|
| Variety | AR | LA | MO | MS | TX | Avg. | AR | LA | MO | MS | TX | Avg. |
| CL172 | 68 | 64 | 65 | 62 | 59 | 64 | 73 | 71 | 72 | 71 | 68 | 71 |
| CL111 | 67 | 62 | 63 | 50 | 64 | 61 | 74 | 73 | 72 | 72 | 71 | 72 |
| CL151 | 68 | 61 | 62 | 57 | 63 | 62 | 74 | 70 | 71 | 71 | 71 | 71 |
| CL162 | 65 | 58 | 50 | 46 | 60 | 56 | 73 | 71 | 69 | 70 | 70 | 70 |
| CL181AR | 64 | 62 | 64 | 54 | 55 | 60 | 72 | 71 | 72 | 70 | 67 | 70 |
| CL142AR | 59 | 57 | 51 | 46 | 59 | 54 | 73 | 70 | 72 | 70 | 69 | 71 |
| CL152 | 67 | 60 | 67 | 60 | 64 | 64 | 73 | 71 | 73 | 70 | 71 | 72 |
| Roy J | 65 | 57 | 62 | 54 | 54 | 58 | 73 | 68 | 73 | 71 | 68 | 71 |
| Francis | 63 | 58 | 61 | 54 | 61 | 59 | 73 | 69 | 73 | 71 | 70 | 71 |
| Wells | 63 | 54 | 58 | 47 | 60 | 56 | 74 | 69 | 72 | 71 | 69 | 71 |
| RU0801081 | 65 | 57 | 59 | 49 | 63 | 59 | 75 | 71 | 72 | 70 | 71 | 72 |

Table 11 shows agronomic characteristics for rice cultivar CL172 and ten other rice cultivars. These data are the mean from the Cooperative Uniform Regional Rice Nursery (URRN) trials conducted in 2012-2013. Column one shows the variety, column two shows the average grain yield in bushels per acre, column three shows the average plant height in inches, column four shows the maturity in days at 50% heading, column five shows the percent lodging and column six shows the milling figures of percent head rice (or whole kernel rice) as compared to the percent of total milled rice (HR-TR). In MO, 10% lodging equals 0% lodging and everything is rated at least 10%. Yield data for 2012 is from AR, LA and MS, and all other characteristics include MO and TX. In 2013, all states are included.

TABLE 11

| Variety | Yield (bu/ac) | Height (in) | Maturity (50% HD) | Lodging % | Milling HR:TR |
|---|---|---|---|---|---|
| CL172 | 197 | 35 | 88 | 2 really 0 | 61-70 |
| CL111 | 202 | 39 | 86 | 14 | 62-71 |

TABLE 11-continued

| Variety | Yield (bu/ac) | Height (in) | Maturity (50% HD) | Lodging % | Milling HR:TR |
|---|---|---|---|---|---|
| CL151 | 208 | 39 | 88 | 15 | 61-71 |
| CL162 | 172 | 42 | 84 | 13 | 56-70 |
| CL181AR | 187 | 36 | 88 | 8 | 60-70 |
| CL142AR | 195 | 43 | 87 | 10 | 54-70 |
| CL152 | 182 | 38 | 87 | 6 | 61-71 |
| Roy J | 204 | 42 | 92 | 10 | 56-70 |
| Francis | 194 | 40 | 88 | 10 | 59-71 |

TABLE 11-continued

| Variety | Yield (bu/ac) | Height (in) | Maturity (50% HD) | Lodging % | Milling HR:TR |
|---|---|---|---|---|---|
| Wells | 195 | 41 | 89 | 7 | 57-71 |
| LaKast | 217 | 42 | 86 | 14 | 59-71 |

Table 12 shows the Riceland Laboratory quality data for rice cultivar CL172 and twelve other rice cultivars. The data are the result of trials at the Arkansas Rice Performance Trials (ARPT) from 2012 from five locations, including Clay County Farmer Field, (CLAY), Corning, Ark.; Northeast Research and Extension Center, (NEREC), Keiser, Ark.; Newport Extension Center, (NEC), Newport, Ark.; Pine Tree Research Station, (PTRS), Colt, Ark.; and Rice Research and Extension Center, (RREC), Stuttgart, Ark. Column one shows the variety, column two shows the percent head rice (HR), column three shows the percent total rice (TR), column four shows the hull yield, column five shows the bran yield, column six shows the percent chalkiness, column seven shows the kernel length in millimeters, column eight shows the kernel width in millimeters, column nine shows the kernel thickness in millimeters, column ten shows the individual kernel weight (KWT) in milligrams, column 11 shows the satake W, which represents whiteness (essential color, although chalky rice can skew this value), column 12 shows the satake MD, which represents milling degree or the amount of bran removal, column 13 shows the gelatinization temperature in degrees Celsius and column 14 shows the length to width ratio.

TABLE 12

| Variety | % HR | % TR | Hull yield | Bran yield | Chalk | Kernel dimensions (mm) | | | KWT (mg) | Satake | | Gel temp (° C.) | L:W ratio |
|---|---|---|---|---|---|---|---|---|---|---|---|---|---|
| | | | | | | Length | Width | Thickness | | W | MD | | |
| CL172 | 65.4 | 71.7 | 16.8 | 11.5 | 0.702 | 7.28 | 2.13 | 1.71 | 21.1 | 43.1 | 105 | 70.47 | 3.41 |
| CL111 | 65.2 | 71.7 | 15.8 | 12.5 | 0.814 | 7.09 | 2.16 | 1.67 | 20.5 | 44.3 | 109 | 70.94 | 3.28 |
| CL142AR | 60.0 | 71.9 | 17.1 | 11.1 | 1.046 | 7.03 | 2.26 | 1.75 | 22.4 | 44.8 | 112 | 70.03 | 3.12 |
| CL151 | 64.7 | 71.4 | 16.4 | 12.1 | 2.002 | 6.77 | 2.18 | 1.70 | 19.7 | 43.7 | 106 | 71.21 | 3.11 |
| CL152 | 65.2 | 71.2 | 15.1 | 13.8 | 1.347 | 6.72 | 1.99 | 1.66 | 17.4 | 39.8 | 89 | 70.27 | 3.37 |
| CL162 | 61.8 | 70.6 | 17.1 | 12.3 | 0.684 | 6.99 | 2.21 | 1.71 | 21.1 | 43.2 | 105 | 70.06 | 3.17 |
| CL181AR | 62.4 | 70.5 | 17.2 | 12.3 | 0.993 | 6.84 | 2.11 | 1.70 | 19.6 | 43.9 | 109 | 71.10 | 3.25 |
| CLXL729 | 61.8 | 70.7 | 17.2 | 12.1 | 2.272 | 6.86 | 2.13 | 1.70 | 19.7 | 46.5 | 119 | 72.63 | 3.22 |
| CLXL745 | 59.5 | 71.8 | 16.5 | 12.0 | 1.176 | 7.11 | 2.20 | 1.70 | 21.3 | 44.9 | 112 | 70.81 | 5.88 |
| Roy J | 64.3 | 72.5 | 16.5 | 11.0 | 0.570 | 7.19 | 2.07 | 1.76 | 20.9 | 42.1 | 100 | 70.11 | 3.48 |
| Francis | 63.8 | 71.9 | 15.9 | 12.2 | 1.036 | 6.68 | 2.05 | 1.66 | 18.3 | 42.3 | 100 | 70.28 | 3.27 |
| Wells | 58.8 | 71.4 | 16.2 | 12.5 | 1.260 | 7.25 | 2.09 | 1.73 | 20.9 | 43.6 | 107 | 70.38 | 3.47 |
| RU0801081 | 62.2 | 71.9 | 15.8 | 12.4 | 0.622 | 7.50 | 2.10 | 1.72 | 21.2 | 43.7 | 107 | 69.92 | 3.58 |

Table 13 shows physical traits for rice cultivar CL172 and twelve other long-grain rice cultivars. The data are the result of trials at the Cooperative Uniform Regional Rice Nursery (URRN) from 2013 for different locations, including Stuttgart, Ark.; Crowley, La.; and Stoneville, Miss. Data was collected using WinSeedle. Column one shows the variety, column two shows the location, column three shows the number of kernels scanned, column four shows the mean kernel length in millimeters plus/minus the LSD, column five shows the mean kernel width in millimeters plus/minus LSD, column six shows the mean length to width ratio plus/minus the LSD and column seven shows the percent chalk.

maximum disease susceptibility, which typically results in complete plant death and/or yield loss. Depending upon the disease in question, a disease rating of four to six is usually indicative of acceptable disease resistance under conditions slightly favoring the pathogen. Numerical ratings are sometimes converted to letter symbols where 0-3=R (resistant), 3-4=MR (moderately resistant), 5-6=MS (moderately susceptible) 7=S (susceptible) and 8-9 VS (very susceptible). Exceptions to established ratings do occur unexpectedly as disease situations change.

Greenhouse blast tests are the primary means of screening large number of entries for varietal reaction to the many blast races occurring in the production areas. Although results are quite variable and testing conditions tends to overwhelm any field resistance present in the entry, this test provides an accurate definition of the fungus-variety genetics. Blast field nurseries, utilizing both natural and lab produced inoculum, are established in an effort to better define blast susceptibility under field conditions. Since field nursery is also quite vari-

TABLE 13

| Variety | Location | No. kernel scanned | Kernel length (mm) | | | Kernel width (mm) | | | L/W ratio | | | % Chalk |
|---|---|---|---|---|---|---|---|---|---|---|---|---|
| | | | Mean | +/– | LSD | Mean | +/– | LSD | Mean | +/– | LSD | |
| CL172 | AR | 123 | 6.88 | +/– | 0.42 | 2.10 | +/– | 0.14 | 3.28 | +/– | 0.21 | 2.63 |
| CL 111 | LA | 122 | 6.78 | +/– | 0.46 | 2.18 | +/– | 0.12 | 3.11 | +/– | 0.19 | 6.76 |
| CL 151 | LA | 128 | 6.32 | +/– | 0.38 | 2.22 | +/– | 0.10 | 2.84 | +/– | 0.17 | 11.22 |
| CL162 | MS | 114 | 6.55 | +/– | 0.41 | 2.22 | +/– | 0.12 | 2.95 | +/– | 0.17 | 6.70 |
| CL 181AR | AR | 115 | 6.64 | +/– | 0.39 | 2.11 | +/– | 0.11 | 3.15 | +/– | 0.21 | 5.45 |
| CL 142AR | AR | 104 | 6.64 | +/– | 0.43 | 2.24 | +/– | 0.12 | 2.97 | +/– | 0.22 | 1.25 |
| CL 152 | LA | 134 | 6.35 | +/– | 0.39 | 2.01 | +/– | 0.11 | 3.17 | +/– | 0.18 | 8.64 |
| Roy J | AR | 123 | 6.79 | +/– | 0.37 | 2.02 | +/– | 0.11 | 3.36 | +/– | 0.23 | 1.44 |
| Francis | AR | 133 | 6.26 | +/– | 0.35 | 2.09 | +/– | 0.10 | 3.00 | +/– | 0.21 | 5.41 |
| Wells | AR | 108 | 6.83 | +/– | 0.43 | 2.12 | +/– | 0.09 | 3.23 | +/– | 0.23 | 2.03 |
| LaKast | AR | 119 | 6.92 | +/– | 0.49 | 2.03 | +/– | 0.12 | 3.41 | +/– | 0.21 | 4.57 |
| Mermentau | LA | 130 | 6.66 | +/– | 0.42 | 2.04 | +/– | 0.10 | 3.27 | +/– | 0.18 | 6.72 |
| Cheniere | LA | 126 | 6.85 | +/– | 0.39 | 2.11 | +/– | 0.12 | 3.25 | +/– | 0.20 | 2.72 |

Disease Evaluations for Rice Cultivar CL172
Greenhouse Blast Tests

Rice diseases are usually rated visually on a 0-9 scale to estimate degree of severity. Numerical data is often converted to this scale. A rating of zero indicates complete disease immunity. A rating of one to three indicates resistance where little loss occurs and in the case of rice blast pathogen growth is restricted considerably. Conversely, a nine rating indicates able, new techniques are currently being developed and evaluated to better estimate cultivar field resistance to blast.

Table 14 shows a summary of available leaf blast rating data from CL172 and eight other rice varieties inoculated with the indicated race using standard greenhouse techniques from trials in 2012 to 2013. Data is shown on the standard visual rating scale of 0-9 where 0=resistant and 9=very susceptible and is also converted into letter symbols. Plants in the 3-r leaf growth stage were sprayed with spore suspension, held in moist chamber 12-18 hours then moved to greenhouse conditions. Column 1 shows the variety and columns two through seventeen show the leaf blast rating data for each race for each variety in the visual rating scale and letter symbol.

TABLE 14

| Variety | IB-1 | IB-1 | IB-49 | IB-49 | IC-17 | IC-17 | IE-1 | IE-1 | IG-1 | IG-1 | ID-13 | ID-13 | IE-1K | IE-1K | IB-33 | IB-33 |
|---|---|---|---|---|---|---|---|---|---|---|---|---|---|---|---|---|
| CL172 | 0 | R | 0 | R | 2 | MR | 0 | R | 0 | R | 0 | R | 5 | MS | 5 | MS |
| CL111 | 0 | R | 6 | S | 3 | MR | 4 | MS | 0 | R | 0 | R | 3 | MR | 5 | MS |
| CL151 | 4 | MR | 6 | S | 6 | S | 7 | S | 0 | R | 0 | R | 6 | S | 7 | S |
| CL152 | 4 | MR | 6 | S | 6 | S | 5 | S | 2 | MR | 2 | MR | 6 | S | 6 | S |
| Roy J | 6 | S | 7 | S | 5 | MS | 6 | S | 6 | S | 4 | MR | 5 | MS | 7 | S |
| Templeton | 0 | R | 1 | R | 0 | R | 0 | R | 0 | R | 0 | R | 2 | MR | 5 | MS |
| Francis | 6 | S | 7 | S | 8 | VS | 6 | S | 6 | S | 4 | MR | 7 | S | 7 | S |
| Wells | 6 | S | 7 | S | 7 | S | 7 | S | 2 | MR | 1 | R | 6 | S | 7 | S |
| LaKast | 5 | MS | 7 | S | 7 | S | 6 | S | 5 | MS | 6 | S | 7 | S | 6 | S |

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Deposit Information

A deposit of the Board of Trustees of the University of Arkansas proprietary Rice Cultivar CL172 disclosed above and recited in the appended claims has been made with the American Type Culture Collection (ATCC), 10801 University Boulevard, Manassas, Va. 20110. The date of deposit was Jan. 15, 2015. The deposit of 2,500 seeds was taken from the same deposit maintained by Board of Trustees of the University of Arkansas since prior to the filing date of this application. All restrictions will be irrevocably removed upon granting of a patent, and the deposit is intended to meet all of the requirements of 37 C.F.R. 1.801-1.809. The ATCC Accession Number is PTA-121909. The deposit will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A seed of rice cultivar CL172, wherein a representative sample of seed of said cultivar has been deposited under ATCC Accession No. PTA-121909.

2. A rice plant, or a part thereof, produced by growing the seed of claim 1.

3. A tissue culture of cells produced from the plant of claim 2, wherein said cells of the tissue culture are produced from a plant part selected from the group consisting of leaf, pollen, embryo, cotyledon, hypocotyl, meristematic cell, root, root tip, pistil, anther, flower, stem, glumes and panicle.

4. A protoplast produced from the plant of claim 2.

5. A protoplast produced from the tissue culture of claim 3.

6. A rice plant regenerated from the tissue culture of claim 3, wherein the plant has all of the morphological and physiological characteristics of rice cultivar CL172.

7. A method for producing an $F_1$ hybrid rice seed, wherein the method comprises crossing the plant of claim 2 with a different rice plant and harvesting the resultant $F_1$ hybrid rice seed.

8. A hybrid rice seed produced by the method of claim 7.

9. A hybrid rice plant, or a part thereof, produced by growing said hybrid rice seed of claim 8.

10. A method of producing an herbicide resistant rice plant, wherein the method comprises transforming the rice plant of claim 2 with a transgene, wherein the transgene confers resistance to an herbicide selected from the group consisting of imidazolinone, sulfonylurea, glyphosate, glufosinate, L-phosphinothricin, triazine and benzonitrile.

11. An herbicide resistant rice plant produced by the method of claim 10.

12. A method of producing an insect resistant rice plant, wherein the method comprises transforming the rice plant of claim 2 with a transgene that confers insect resistance.

13. An insect resistant rice plant produced by the method of claim 12.

14. The rice plant of claim 13, wherein the transgene encodes a *Bacillus thuringiensis* endotoxin.

15. A method of producing a disease resistant rice plant, wherein the method comprises transforming the rice plant of claim 2 with a transgene that confers disease resistance.

16. A disease resistant rice plant produced by the method of claim 15.

17. A method of producing a rice plant with modified fatty acid metabolism or modified carbohydrate metabolism, wherein the method comprises transforming the rice plant of claim 2 with a transgene encoding a protein selected from the group consisting of fructosyltransferase, levansucrase, alpha-amylase, invertase and starch branching enzyme or DNA encoding an antisense of stearyl-ACP desaturase.

18. A rice plant having modified fatty acid metabolism or modified carbohydrate metabolism produced by the method of claim 17.

19. A method of introducing a desired trait into rice cultivar CL172, wherein the method comprises:
(a) crossing a CL172 plant, wherein a representative sample of seed was deposited under ATCC Accession No. PTA-121909, with a plant of another rice cultivar that comprises a desired trait to produce progeny plants, wherein the desired trait is selected from the group consisting of male sterility, herbicide resistance, insect resistance, abiotic stress tolerance, modified fatty acid metabolism, modified carbohydrate metabolism and resistance to bacterial disease, fungal disease or viral disease;
(b) selecting one or more progeny plants that have the desired trait;
(c) backcrossing the selected progeny plants with the CL172 plants to produce backcross progeny plants;
(d) selecting for backcross progeny plants that have the desired trait; and
(e) repeating steps (c) and (d) three or more times to produce selected fourth or higher backcross progeny plants that comprise the desired trait.

20. A plant produced by the method of claim 19, wherein the plant has the desired trait and all of the physiological and morphological characteristics of rice cultivar CL172.

21. The plant of claim 20, wherein the desired trait is herbicide resistance and the resistance is conferred to an herbicide selected from the group consisting of imidazolinone, sulfonylurea, glyphosate, glufosinate, L-phosphinothricin, triazine and benzonitrile.

22. The plant of claim 20, wherein the desired trait is insect resistance and the insect resistance is conferred by a transgene encoding a *Bacillus thuringiensis* endotoxin.

23. The plant of claim 20, wherein the desired trait is modified fatty acid metabolism or modified carbohydrate metabolism and said desired trait is conferred by a nucleic acid encoding a protein selected from the group consisting of fructosyltransferase, levansucrase, alpha-amylase, invertase and starch branching enzyme or DNA encoding an antisense of stearyl-ACP desaturase.

24. A method for controlling weeds in the vicinity of a rice plant of rice cultivar CL172, said method comprising applying an effective amount of at least one acetohydroxyacid synthase (AHAS)-inhibiting herbicide to the weeds and to the rice plant, wherein a representative sample of seed of said cultivar was deposited under ATCC Accession No. PTA-121909.

25. The method of claim 24, wherein said AHAS-inhibiting herbicide is selected from the group consisting of an imidazolinone herbicide, a sulfonylurea herbicide, a triazolopyrimidine herbicide, a pyrimidinyloxybenzoate herbicide, a sulfonylamino-carbonyltriazolinone herbicide, and a mixture thereof.

26. The method of claim 25, wherein said imidazolinone herbicide is selected from the group consisting of: [2-(4-isopropyl-4-methyl-5-oxo-2-] imidiazolin-2-yl)-nicotinic acid, 2-(4-isopropyl)-4-methyl-5-oxo-2-imidazolin-2-yl)-3-quinolinecarboxylic acid, [5-ethyl-2-(4-isopropyl-4-methyl-] 5-oxo-2-imidazolin-2-yl)-nicotinic acid, 2-(4-isopropyl-4-methyl-5-oxo-2-imidazolin-2-yl)-5-(methoxymethyl)-nicotinic acid, 2-(4-isopropyl-4-methyl-5-oxo-2-imidazolin-2-yl)-5-methylnicotinic acid, and a mixture of methyl 6-(4-isopropyl-4-methyl-5-oxo-2-imidazolin-2-yl)-m-toluate, methyl [2-(4-] isopropyl-4-methyl-5-oxo-2-imidazolin-2-yl)-p-toluate, and mixture thereof.

27. The method of claim 24, wherein said AHAS-inhibiting herbicide is an imidazolinone herbicide or a mixture of two or more imidazolinone herbicides.

28. A seed of rice cultivar CL172, wherein said seed is treated with an AHAS-inhibiting herbicide, and wherein a representative sample of seed of said cultivar was deposited under ATCC Accession No. PTA-121909.

29. The seed of claim 28, wherein said AHAS-inhibiting herbicide is selected from the group consisting of an imidazolinone herbicide, a sulfonylurea herbicide, a triazolopyrimidine herbicide, a pyrimidinyloxybenzoate herbicide, and a sulfonylamino-carbonyltriazolinone herbicide, or mixture thereof.

30. The seed of claim 28, wherein said AHAS-inhibiting herbicide is an imidazolinone herbicide or a mixture of two or more imidazolinone herbicides.

31. A method for combating undesired vegetation comprising contacting a seed of rice cultivar CL172 before sowing and/or after pregermination with an AHAS-inhibiting herbicide, wherein a representative sample of seed of said cultivar was deposited under ATCC Accession No. PTA-121909.

32. The method of claim 31, wherein said AHAS-inhibiting herbicide is selected from the group consisting of an imidazolinone herbicide, a sulfonylurea herbicide, a triazolopyrimidine herbicide, a pyrimidinyloxybenzoate herbicide, and a sulfonylamino-carbonyltriazolinone herbicide, or mixture thereof.

33. The method of claim 31, wherein said AHAS-inhibiting herbicide is an imidazolinone herbicide or a mixture of two or more imidazolinone herbicides.

34. A method for producing an herbicide-resistant rice plant comprising crossing a first rice plant that is a rice plant of rice cultivar CL172 with a second rice plant that is not resistant to an herbicide, wherein a representative sample of seed of said cultivar was deposited under ATCC Accession No. PTA-121909.

35. The method of claim 34 further comprising selecting for a progeny rice plant that is resistant to at least one AHAS-inhibiting herbicide.

36. The method of claim 35, wherein said AHAS-inhibiting herbicide is an imidazolinone herbicide or a mixture of two or more imidazolinone herbicides.

37. An herbicide-resistant rice plant produced by the method of claim 34.

38. A method for increasing the herbicide-resistance of a plant comprising crossing a first rice plant that is a rice plant of rice cultivar CL172 with a second rice plant, wherein a representative sample of seed of said cultivar was deposited under ATCC Accession No. PTA-121909.

39. The method of claim 38 further comprising selecting for a progeny rice plant that comprises increased herbicide resistance to at least one AHAS-inhibiting herbicide when compared to the herbicide resistance of said second rice plant.

40. The method of claim 39, wherein said AHAS-inhibiting herbicide is an imidazolinone herbicide or a mixture of two or more imidazolinone herbicides.

41. A plant produced by the method of claim 38.

* * * * *